United States Patent
Toyoshima et al.

(10) Patent No.: US 8,206,980 B2
(45) Date of Patent: Jun. 26, 2012

(54) METHOD FOR CULTIVATION OF HAIR FOLLICULAR DERMAL SHEATH CELLS

(75) Inventors: Koei Toyoshima, Hiroshima (JP);
Mikaru Matsunaga, Hiroshima (JP);
Katsutoshi Yoshizato, Hiroshima (JP)

(73) Assignees: Phoenixbio Co., Ltd., Hiroshima (JP);
Biointegrence Inc., Hiroshima (JP)

( * ) Notice: Subject to any disclaimer, the term of this patent is extended or adjusted under 35 U.S.C. 154(b) by 996 days.

(21) Appl. No.: 11/992,753

(22) PCT Filed: Oct. 2, 2006

(86) PCT No.: PCT/JP2006/319728
§ 371 (c)(1),
(2), (4) Date: Aug. 4, 2008

(87) PCT Pub. No.: WO2007/037486
PCT Pub. Date: Apr. 5, 2007

(65) Prior Publication Data
US 2010/0197019 A1      Aug. 5, 2010

(30) Foreign Application Priority Data
Sep. 30, 2005   (JP) ................................. 2005-289012

(51) Int. Cl.
*C12N 5/071*   (2010.01)
*C12N 5/074*   (2010.01)
*C12N 5/00*    (2006.01)
*C12N 5/02*    (2006.01)

(52) U.S. Cl. ........ 435/377; 435/325; 435/371; 435/373; 435/405

(58) Field of Classification Search .......................... None
See application file for complete search history.

(56) References Cited

U.S. PATENT DOCUMENTS
2006/0088505 A1   4/2006   Hoffmann et al.

FOREIGN PATENT DOCUMENTS
| EP | 1 702 632 | 9/2006 |
| WO | 03/104443 | 12/2003 |
| WO | 2005/053763 | 6/2005 |
| WO | 2005/059119 | 6/2005 |

OTHER PUBLICATIONS

G. D. Richardson et al., "Cultured Cells from the Adult Human Hair Follicle Dermis can be Directed Toward Adipogenic and Osteogenic Differentiation", J. Invest. Dermatol., vol. 124, No. 5, pp. 1090-1091, May 2005.
J. Cab et al., "Hair Follicle Dermal Cells Differentiate into Adipogenic and Osteogenic Lineages", Experimental Dermatology, vol. 12, pp. 849-859, 2003.
M. Lako et al., "Hair Follicle Dermal Cells Repopulate the Mouse Haematopoietic System", Journal of Cell Science, vol. 115, No. 20, pp. 3967-3974, 2002.
L. V. Goodman et al., "Secretion of Stromelysin by Cultured Dermal Papilla Cells: Differential Regulation by Growth Factors and Functional Role in Mitogen-Induced Cell Proliferation", Journal of Cellular Physiology, vol. 151, pp. 41-49, 1992.
C. Schollmann et al., "Basic Fibroblast Growth Factor Modulates the Mitogenic Potency of the Platelet-Derived Growth Factor (PDGF) Isoforms by Specific Up-Regulation of the PDGF α Receptor in Vascular Smooth Muscle Cells", The Journal of Biological Chemistry, vol. 267, No. 25, pp. 18032-18039, Sep. 5, 1992.
K. J. McElwee et al., "Cultured Peribulbar Dermal Sheath Cells Can Induce Hair Follicle Development and Contribute to the Dermal Sheath and Dermal Papilla", J. Invest. Dermatol., vol. 121, No. 6, pp. 1267-1275, Dec. 2003.

*Primary Examiner* — Daniel C Gamett
(74) *Attorney, Agent, or Firm* — Wenderoth, Lind & Ponack, L.L.P.

(57) ABSTRACT

A method for culture of hair follicular dermal sheath cells or precursor cells thereof which are potent cellular materials for such as hair regeneration by cell transplantation is provided. That is, by performing culture in an animal cell culture medium supplemented with platelet-derived growth factor AA (PDGF-AA) and fibroblast growth factor 2 (FGF2), hair follicular dermal sheath cells are proliferated while sustaining their function, or hair follicular dermal sheath precursor cells are differentiated into dermal sheath cells and proliferated.

7 Claims, 10 Drawing Sheets

A

B

METHOD FOR CULTIVATION OF HAIR FOLLICULAR DERMAL SHEATH CELLS

This application is a U.S. national stage of International Application No. PCT/JP2006/319728 filed Oct. 2, 2006.

TECHNICAL FIELD

The present invention relates to a method for cultivation of hair-follicular dermal sheath cells. More particularly, the present invention relates to a culture method capable of proliferating hair follicular dermal sheath cells while maintaining their function. Still more particularly, the present invention relates to a culture method capable of differentiating hair follicular dermal sheath precursor cells into dermal sheath cells and proliferating the cells.

BACKGROUND ART

A hair follicle, a tissue producing hair, is formed in a certain period of the embryonic stage by an interaction between a special mesenchyme and the epidermis called a dermal condensation. Cells constituting such a dermal condensation become a dermal papilla after hair follicle formation is completed. The dermal papilla also deeply participates in the progression of hair cycle which is a cycle of anagen and telogen of hair. In order to induce hair follicle formation by cell transplantation, this interaction between the epidermis and dermal papilla (mesenchyme) should be allowed to take place in the living body. The present inventors have invented a method for growing hair shafts from this hair follicles as a means for allowing hairs to grow on a hairless area on the skin in which mixed epidermal and dermal papilla cells are transplanted in the skin, whereby the human dermal papilla cells induce the epidermal cells into a hair follicles, and hair shafts are allow to grow from this hair follicles, and have already applied for patent (Patent document 1).

Further, it has been reported that dermal papilla cells isolated from rat whiskers and primary cultured can be subcultured for a long period of time by adding a supernatant of conditioned medium of primary culture of rat sole epidermal cells, and the dermal papilla cells subcultured for a long period of time sustain an ability to induce hair follicle formation (Non-patent document 1, Patent document 2). However, the present inventors have shown that the rat whisker-derived dermal papilla cells proliferated by long-term subculture (for about more than 40 passages) using the method described in Patent document 2 sustain an ability to induce hair follicle formation, but an ability to grow hair shafts from the hair follicles whose formation has been induced is reduced and lost (Patent document 1). As a method for solving this problem, the present inventors have made it possible to restore the reduced ability to induce hair growth by adding a given amount of dermal sheath cells of hair follicles to dermal papilla cells whose ability to grow hair shafts has been reduced due to long-term subculture, and to significantly promote the growth of hair emerging from the hair follicles, and have applied for patent (Patent document 1).

It is defined that the dermal sheath is a tissue composed of one or several dermal cell layer(s) (positive to vimentin) surrounding the outermost layer of the hair follicle, and is distributed in the lower one-third or less of the hair follicle, and is composed of smooth muscle-α-actin (α-SMA) positive cells. This dermal sheath is histologically continuous with the dermal papilla at the lowest end of the hair bulb. Further, when the rat whisker hair follicle is cut above and below and hair follicular dermal sheath cells of the hair bulb are transplanted by implantation in the upper part of the hair follicle, the hair bulb including dermal papilla derived from the hair follicular dermal sheath cells is reconstructed and elongation of hair shaft is observed. From these events, it has been indicated that precursor cells of dermal papilla cells are distributed in the hair follicular dermal sheath, and are a supply source of cells to the dermal papilla (Non-patent document 3).

It has been reported that based on these findings, when the hair follicular dermal sheath of a male was cross-transplanted in the skin of a forearm area of a female, the formation of the hair follicle including the dermal papilla derived from the transplanted dermal sheath was induced, and hair was allowed to grow (Non-patent document 4). Further, it has been reported that when primary cultured rat hair follicular dermal sheath cells were allografted in just under the epidermis of a hairless skin area of the rat auricle, the hair follicle formation was induced from the epidermis of the auricle, resulting in hair growth (Non-patent document 5). From these events, hair follicular dermal sheath cells include precursor cells of dermal papilla cells and can be used as a supply source of the dermal papilla cells.

Further, it has been reported that hair follicular dermal sheath cells are promising not only as a supply source of dermal papilla cells, but also as a wound healing material (Non-patent documents 6 and 7, Patent document 3). In a study using a rat, when cultured hair follicular dermal sheath cells derived from a whisker were transplanted in the dorsal area of a nude mouse in combination with cells prepared from the hair follicular outer root sheath, normal skin was formed. Further, when the epidermis formation of bell-type artificial skin composed of human cells and collagen gel was compared between fibroblasts derived from human foreskin and hair follicular dermal sheath cells derived from scalp hair follicles, and as a result, apparently, a thicker epidermal layer was formed when hair follicular dermal sheath cells were used. From this, it can be said that dermal sheath cells have an ability to differentiate not only into the dermal papilla but also into fibroblasts which form good dermis.

As described above, hair follicular dermal sheath cells can be used for improvement of the quality in hair follicle regeneration, and as a supply source of dermal papilla cells and fibroblasts of artificial skin. Further, because the cells have a function of promoting elongation of the hair shafts, it can be said that the cells have an extremely high utility value in the development of pharmaceuticals such as hair growth agents and therapeutic agents for alopecia targeting the hair follicular dermal sheath cells. However, the human hair follicular dermal sheath is a small tissue surrounding the hair follicle with almost a single layer of cells, and the number of obtained cells is extremely small. Further, with a conventional culture method, the proliferation rate of hair follicular dermal sheath cells in primary culture is extremely low. Generally, in the case where the proliferation rate in primary culture is low, the risk of contamination by fungi and bacteria becomes very high, and it becomes difficult to secure a cell number that enables the application thereof to a treatment or development of pharmaceuticals. Accordingly, a culture method in which primary culture with a small amount of hair follicular dermal sheath tissue at a proliferation rate as high as possible is carried out and then, cells which sustain a definite function can be secured in sufficient quantity has been demanded. However, it has been confirmed that the rat hair follicular dermal sheath cells subjected to primary culture have an ability to induce the hair follicle and to grow hair so far, but it has not been confirmed that cells proliferated by subculture using a conventional culture technique have a significant ability to induce the hair follicle and to grow hair or ability to form the hair follicular dermal sheath (Non-patent document 5).

As discussed in the above, by culturing and propagating cells having a specific function while sustaining a definite function, cells having a high utility value can be obtained in a large amount. However, if the differentiation of pluripotent stem cells or precursor cells into cells which are capable of differentiating into a specific cell species and have a high proliferation potential can be controlled by culture, not only a similar result can be obtained, but also targeted cells can be efficiently obtained from a small amount of tissue or cells. On the other hand, dermal sheath cells disappear in the telogen phase in hair cycle, therefore, the existence of precursor cells thereof can be expected. However, there has been no report so far of the existence of the precursor cells or a culture method for the precursor cells.

Generally, in a cell culture method, various growth factors are added to a culture medium and proliferation and differentiation of cells are controlled. It has been reported that dermal sheath cells are precursor cells of dermal papilla cells, and a culture method with the addition of various growth factors has been reported. Among them, there are reports that the addition of fibroblast growth factor 2 (FGF2) or a supernatant of epidermal cell culture is effective in cell proliferation (Non-patent documents 1 and 9). Further, in cultured dermal papilla cells, a subtype of platelet-derived growth factor (PDGF), PDGF-AA does not promote proliferation, but PDGF-BB promotes proliferation in a concentration dependent manner. However, both subtypes of PDGF promote the proliferation of cultured fibroblasts, therefore, it cannot be said that PDGF-BB specifically promotes the proliferation activity of dermal papilla cells. Further, the function of these proliferated cultured dermal papilla cells is not clearly shown. The present inventors have enabled the proliferation of dermal papilla cells that sustain an ability to induce hair follicle formation using the method described in Patent document 2. However, it is difficult to effect culture and proliferation of hair follicular dermal sheath cells using the same method. In the method of Patent document 1, rat whisker-derived hair follicular dermal sheath cells were sufficiently proliferated using a culture medium supplemented with FGF2, and the resulting cultured rat hair follicular dermal sheath cells did not have an ability to induce hair growth alone, but showed a significant ability to grow hair by the addition thereof to dermal papilla cells. However, in human scalp hair-derived hair follicular dermal sheath cells, sufficient cell proliferation cannot be obtained even if a culture medium supplemented with FGF2 is used.

As described above, hair follicular dermal sheath cells are potent cellular materials for such as hair regeneration by cell transplantation, however, there has been no means for well proliferating such hair follicular dermal sheath cells while sustaining their function so far. Further, there has been no report so far of the existence of precursor cells of dermal sheath cells. However, it is apparent that a culture method capable of proliferating newly found dermal sheath precursor cells while sustaining a high proliferation activity and an ability to differentiate into dermal sheath and dermal papilla cells has an extremely high applicability and utility value.

Patent document 1: International Pamphlet for PCT/JP 2004/018421
Patent document 2: JP-A-7-274950
Patent document 3: JP-T-2002-507132
Non-patent document 1: Inamatsu, M. et al., Establishment of rat dermal papilla cell lines that sustain the potency to induce hair follicles from afollicular skin. J. Invest. Dermatol, 111; 767-775, 1998
Non-patent document 2: Weinberg W C et al., Reconstitution of hair follicle development in vivo; determination of follicle formation, hair growth, and hair quality by dermal cells. J. invest. Dermatol., 100, 229-236, 1993
Non-patent document 3; Horne K A and Jahoda C A B, Restoraction of hair growth by surgical implantation of follicular dermal sheath. Development 116, 563-571, 1992
Non-patent document 4: Reynolds A J et al., Trans-gender induction of hair follicles. Nature, 402, 33-34, 1999
Non-patent document 5: McElwee K J et al., Cultured peribulbar dermal sheath cells can induce hair follicle development and contribute to the dermal sheath and dermal papilla. J. invest. Dermatol, 121, 1267-1275, 2003
Non-patent document 6; Jahoda C A B and Reynolds A J, Hair follicle dermal sheath cells: unsung participants in wound healing. Lancet, 358, 1445-1448, 2001
Non-patent document 7: Gharzi A et al., Plasticity of hair follicle dermal cells in wound healing and induction. Exp. Dermatol, 12, 126-136, 2003
Non-patent document 8: Goodman L V and Ledbetter S R, Secretion of stromelysin by cultured dermal papilla cells: differential regulation by growth factors and functional role in mitogen-induced cell proliferation. J. Cellular Physiol, 151, 41-49, 1992
Non-patent document 9: Dawen Yu et al., Expression profiles of tyrosine kinases in cultured follicular papilla cells versus dermal fibroblasts, J. Invest. Dermatol, 123, 283-290, 2004
Non-patent document 10; Jahoda C A B et al., Smooth muscle a-actin is a marker for hair follicle dermis in vivo and in vitro. J. Cell Science, 99, 627-636, 1991
Non-patent document 11: A quantitative study of the differential expression of alpha-smooth muscle actin in cell populations of follicular and non-follicular origin. J. invest. Dermatol. 101, 577-583, 1993
Non-patent document 12: Oliver R F, Histological studies of whisker regeneration in the hooded rat. J. Embryol. exp. Morph., vol. 16, 2, 231-244, October 1966
Non-patent document 13: Oliver R F, Ectopic regeneration of whiskers in the hooded rat from implanted lengths of vibrissa follicle wall. J. Embryol. exp. Morph., vol. 17, 1, 27-34, February 1967

DISCLOSURE OF THE INVENTION

For regenerating tissue by cell transplantation, it is necessary to proliferate the transplanted cells while sustaining the original function of the cells. This results in reducing the amount of tissue extirpated from a patient thereby reducing a burden of the patient. Further, in a similar manner, if the differentiation of differentiation pluripotent stem cells or precursor cells into transit amplifying cells (TA cells) which are capable of differentiating into a specific cell species and have a high proliferation potential can be controlled by cultivation, desired cells can be efficiently obtained from a small amount of tissue or cells.

Hair follicular dermal sheath cells are potent cellular materials for such as hair regeneration by cell transplantation as described above, however, there has been no means for well proliferating such hair follicular dermal sheath cells while sustaining their function so far. In addition, there has been no report so far of the existence of precursor cells of dermal sheath cells. However, a culture method capable of proliferating newly found dermal sheath precursor cells while maintaining a high proliferation activity and an ability to differentiate into dermal sheath and dermal papilla cells has an extremely high applicability and utility value.

An object of the present invention is to provide a method for culture of cells with which not only hair follicular dermal sheath cells and precursor cells thereof can be proliferated but also the cells are allowed to sustain their specific function or to exhibit their function by differentiating them.

The present invention is directed to a culture method for proliferating hair follicular dermal sheath cells while sustaining their function, which comprises culturing the hair follicular dermal sheath cells in an animal cell culture medium supplemented with platelet-derived growth factor AA (PDGF-AA) and fibroblast growth factor 2 (FGF2).

A preferred embodiment of the above invention is that the hair follicular dermal sheath cells are from the dermal sheath in the lower part of the hair follicle are used.

Another embodiment of the above invention is that the animal cell culture medium is Dulbecco's modified Eagle medium supplemented with 1% to 30% serum (DMEM10).

Still another embodiment of the above invention is that the hair follicular dermal sheath cells are cultured with other cells capable of forming the hair follicle.

The present invention is also directed to a culture method for differentiating hair follicular dermal sheath precursor cells into dermal sheath cells and proliferating the cells, which comprises culturing the hair follicular dermal sheath precursor cells in an animal cell culture medium supplemented with platelet-derived growth factor AA (PDGF-AA) and fibroblast growth factor 2 (FGF2).

One embodiment of the above invention is that the hair precursor cells of dermal sheath are from the dermal sheath in the lower part of the hair follicle are used.

Another embodiment of the above invention is that the animal cell culture medium is Dulbecco's modified Eagle medium supplemented with 1% to 30% serum (DMEM10) is used.

Further, the present invention is directed to a precursor cells of dermal sheath which are capable of differentiating into a dermal sheath cells by culturing the cells in an animal cell culture medium supplemented with platelet-derived growth factor AA (PDGF-AA) and fibroblast growth factor 2 (FGF2).

Definition Of Words And Terms

The "function" to be sustained when hair follicular dermal sheath cells are cultured means a function as a supply source of dermal papilla cells, a function of inducing formation of hair follicles having an ability to grow hair, a function of forming the epidermis when skin transplantation is performed or the like.

The "proliferation" of hair follicular dermal sheath cells means that the number of cells which are initially provided for culture is increased by two times or more, preferably 10 times or more, more preferably 100 times or more. Further, the "culture" as used herein includes "primary culture" in which hair follicular dermal sheath cells isolated from the skin are cultured, and "subculture" in which cells proliferated by this primary culture are isolated from the culture medium and culture is continued in a fresh culture medium.

It is defined that the "dermal sheath (DS)" is a tissue composed of one layer or several layers of dermal cells (positive to vimentin) surrounding the outermost layer of the hair follicle, and is distributed in the lower one-half or less of the hair follicle, and is composed of anti-smooth muscle-α-actin (α-SMA) antibody positive cells. This dermal sheath is histologically continuous with the dermal papilla at the lowest end of the hair bulb (Non-patent documents 10 and 11). Further, the dermal sheath in the lower one-third or less of the hair follicle has an ability to differentiate into the dermal papilla and to induce regeneration of the hair bulb, therefore, the dermal sheath cells are considered to be precursor cells of dermal papilla cells. However, there are no cells to which this definition applies in the telogen phase in hair cycle.

The "upper dermal sheath (upper DS)" is a site newly defined in the present invention. It is a tissue composed of one layer or several layers of dermal cells (positive to vimentin) surrounding the outermost layer of the hair follicle, and is distributed by lining the bulge region of ORS and up to the upper area thereof, and is composed of anti-α-SMA antibody-negative cells. In the histological observation, it appears that it is continuous with the cell layer defined as the dermal sheath. It has been reported that the upper DS does not have an ability to induce regeneration of the dermal papilla and regeneration of the hair bulb (Non-patent documents 12 and 13). In the case of rats, it can be obtained by making a cut in the upper side of an arrector pili muscle attached site and the lower side of the blood sinus. In the case of humans, a cut is made at a position one-half the total length of the hair follicle.

The definition of "lower dermal sheath (lower DS)" is made with respect to the newly defined "upper DS", and the conventionally defined DS is defined as the lower DS. The definition of a marker, distribution and the like are the same as those of the above-mentioned dermal sheath.

The "hair bulb" means a bulbous part at the lower end of the hair follicle, and contains dermal papilla, dermal sheath and hair matrix cells. The dermal sheath connects to the dermal papilla at the lowest end of the hair bulb. The lower DS distributed in the hair bulb region is called dermal sheath cup (DSC).

The "induction of hair follicle formation" refers to a phenomenon in which dermal papilla cells induce epidermal cells to form the structure of the hair follicle.

The "induction of hair growth" refers to a phenomenon in which hair matrix cells of the hair follicle differentiate and proliferate thereby forming the hair shaft, and dermal sheath cells act on the hair matrix or ORS to elongate the hair shaft from the body surface.

EFFECTS OF THE INVENTION

According to the method of the present invention, hair follicular dermal sheath cells useful as transplantation cells for such as hair regeneration can be propagated in a large amount while maintaining their function.

Further, the method of the present invention is also effective in proliferating other cells capable of forming the hair follicles (for example, dermal papilla cells) while sustaining their function (for example, an effect equivalent to that of the method of Patent document 2) and is capable of well proliferating hair follicular dermal sheath cells and dermal papilla cells both of which are useful as transplantation cells for such as hair regeneration while sustaining their respective functions. This enables the use of a mixture of both hair follicular dermal sheath cells and dermal papilla cells proliferated together in transplantation for hair regeneration without separating the hair follicular dermal sheath cells and the dermal papilla cells from one another which are contained in an extremely small tissue area.

Further, according to the present invention, a novel hair follicular dermal sheath precursor cell having an ability to differentiate into a hair follicular dermal sheath cells and a culture method capable of differentiating this precursor cell into a hair follicular dermal sheath cells and proliferating the cells can be provided. Accordingly, for example, when cells for transplantation are prepared for such as hair regeneration, the hair follicle tissue isolated from a patient can be more effectively utilized.

BEST MODE FOR CARRYING OUT THE INVENTION

Figure 1:
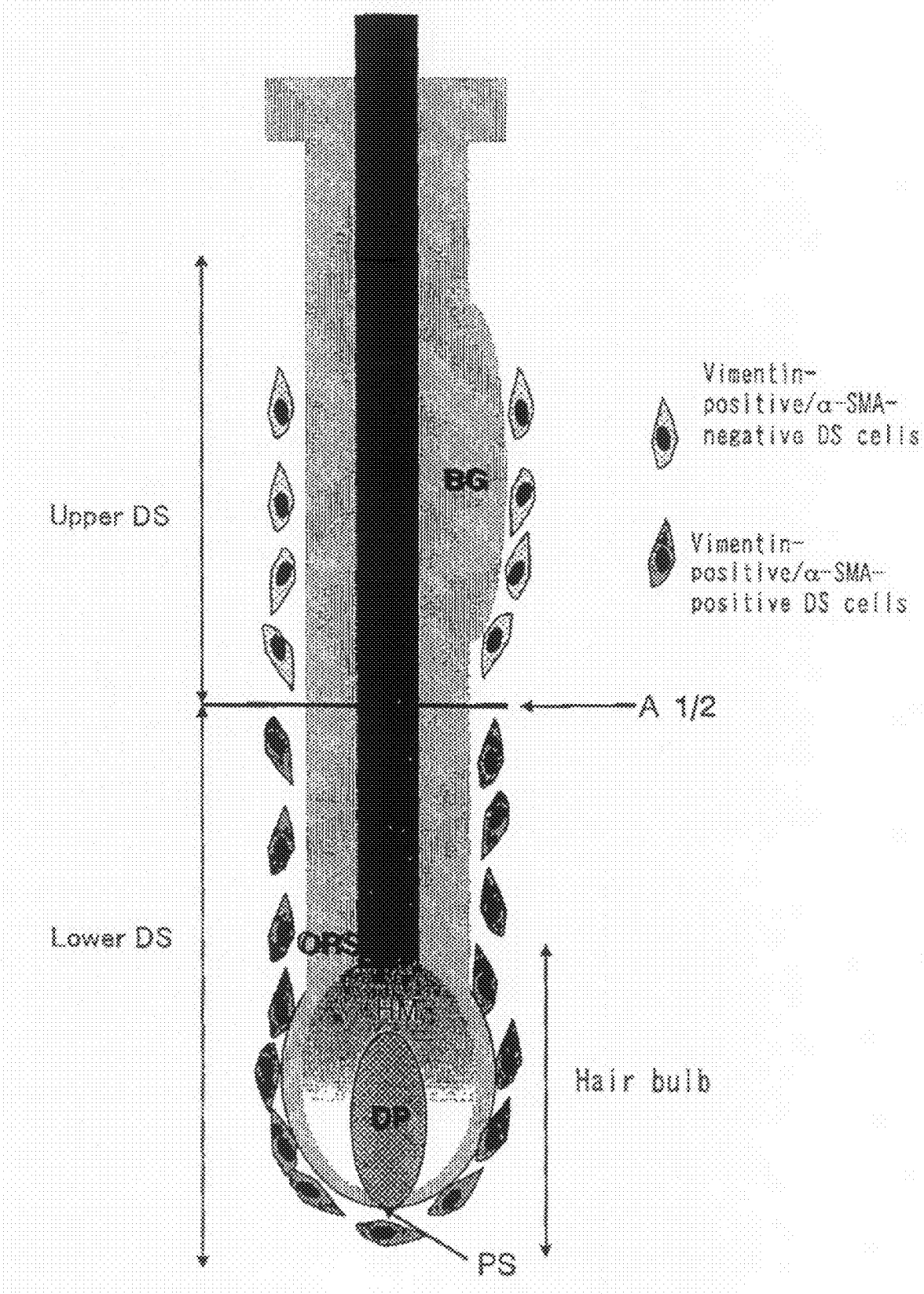
FIG. 1 is a schematic view of a human head hair. A slightly bulbous part at the lower end of the hair follicle is called a hair bulb. In the hair bulb area, the hair matrix (HM) composed of epidermal cells, the dermal papilla (DP) composed of dermal cells surrounded by the hair matrix are included. This dermal papilla connects to the dermal sheath (DS) composed of dermal cells surrounding the outermost layer of the hair follicle at the papillary stalk (PS) at the lowest end of the hair bulb. DS and DP cells express vimentin, which is a marker for dermal cells. Further, it has been defined so far that DS is distributed in the lower one-half of the hair follicle (A ½) and in the lower side of the bulge region, and is positive to anti-smooth muscle-α-actin (α-SMA) antibody. In the present invention, cells which are distributed such that the cells surround the bulge region (BG) in the upper one-half of the hair follicle and are negative to anti-α-SMA antibody and positive to vimentin were defined to be upper DS cells, and cells which are distributed in the lower one-half of the hair follicle and are positive to anti-α-SMA antibody and positive to vimentin were defined to be lower DS cells for the sake of convenience. In the present patent, DP and lower DS were prepared by isolating the hair bulb from the hair follicle, removing the hair matrix (HM) and outer root sheath (ORS), and further separating DP and DS in the lower part of the hair follicle at a position of the papillary stalk (PS) using an ophthalmic surgical knife. Further, the hair follicle was cut above and below at a position of the arrow A, and the upper part of the hair follicle was subjected to an enzyme treatment and then ORS containing upper DS and bulge (BG) and the hair shaft (ES) were separated and obtained using microforceps under a microscope.

FGF2 and PDGF-AA to be added in a culture medium in the method of the present invention are preferably those derived from the same animal species from which cells to be cultured are derived. In the case where human-derived cells are used, FGF2 and PDGF-AA are preferably human-derived substances. Further, FGF2 and PDGF-AA are preferably those produced from a recombinant obtained by a known method or the blood. As human-derived FGF2 and PDGF-AA, commercially available products can be used, respectively (for example, human FGF2 is available from UPSTATE, human-derived PDGF-AA is available from R&D Systems, and so on).

As the culture medium, a known animal cell culture medium, for example, Alpha-MEM (Dainippon Pharma. Co., Ltd., etc.), ATCC-CRCM 30 (ATCC), Coon's modified F12 (SIGMA, etc.), DM-160 and DM-201 (Nihon Pharmaceutical Co., Ltd.), Doulbecco's modified Eagle's Medium (DMEM) with High Glucose (4500 mg/L) (Dainippon Pharma. Co., Ltd., etc.), Doulbecco's modified Eagle's Medium (DMEM) with Low Glucose (1000 mg/L) (Wako Pure Chemical Industries, Ltd., etc.), DMEM:Ham's F12 mixed medium (1:1) (Dainippon Pharma. Co., Ltd., etc.), DMEM:RPMI 1640 mixed medium (1:1), Eagles basal medium (BME) (Dainippon Pharma. Co., Ltd., etc.), Eagle's Minimum Essential Medium (EMEM) (Dainippon. Pharma. Co., Ltd., etc.), EMEM:RPMI 1640 mixed medium (1:1), ES medium (Nissui Pharmaceutical Co., Ltd.), Fischer's Medium (Wako Pure Chemical Industries, Ltd., etc.), Ham's F10 (Dainippon Pharma. Co., Ltd., etc.), Ham's F12 medium (Dainippon Pharma. Co., Ltd., etc.), Ham's F12:RPMI 1640 mixed medium (1:1), Kaighns modification of Ham's F12 (F12K) (Dainippon Pharma. Co., Ltd., etc.), Leibovitz's L-15 medium (Dainippon Pharma. Co., Ltd., etc.), McCoy's 5A (Dainippon Pharma. Co., Ltd., etc.), RITC 80-7 medium (Research Institute for the Functional Peptides Co., Ltd.), HF-C1 medium (Research Institute for the Functional Peptides Co., Ltd.), MCDB 107 medium (Research Institute for the Functional Peptides Co., Ltd.), MCDB 201 medium (SIGMA), HSMC-C1 medium (Research Institute for the Functional Peptides Co., Ltd.), HEC-C1 medium (Research Institute for the Functional Peptides Co., Ltd.), MCDB 131 medium (Research Institute for the Functional Peptides Co., Ltd.), HSMC-C2 medium (Research Institute for the Functional Peptides Co., Ltd.), MCDB 153 medium (Research Institute for the Functional Peptides Co., Ltd.), MCDB 153 HAA medium (Research Institute for the Functional Peptides Co., Ltd.), Medium 199 (Dainippon Pharma. Co., Ltd., etc.), NCTC 135 (Dainippon Pharma. Co., Ltd., etc.), RPMI 1640 (Dainippon. Pharma. Co., Ltd., etc.), Waymouth's MB 752/1 medium (Dainippon Pharma. Co., Ltd., etc.), Williams' medium E (Dainippon Pharma. Co., Ltd., etc.), and the like can be exemplified. In the case where such a culture medium is a serum-free medium, serum is added in an amount of about 1% to 30%. Further, in the case where the cells to be cultured are human-derived cells, it is preferred to use human-derived serum.

The addition amount of FGF2 to such an animal cell culture medium is from 0.5 to 20 ng/ml, preferably from 2 to 20 ng/ml, and the addition amount of PDGF-AA is from 0.5 to 20 ng/ml, preferably from about 2 to 20 ng/ml, and FGF2 with PDGF-AA can be combined within these ranges.

The hair follicular dermal sheath to be cultured preferably includes the hair bulb. Further, the hair follicular dermal sheath is positive to anti-α-SMA antibody, and is preferably derived from head hair, whiskers or body hair. It is possible to simultaneously culture hair follicular dermal sheath cells and other cells capable of forming the hair follicle, and in this case, the cells capable of forming the hair follicle are preferably dermal papillae. The dermal papilla cells are also preferably derived from head hair, whiskers or body hair.

Further, the hair follicular dermal sheath precursor cells can be prepared from, for example, upper one-half of the hair follicle. It is preferred to include a region contacted with the bulge. Further, the hair follicular dermal sheath precursor cells are negative to anti-α-SMA antibody, and are preferably derived from head hair, whiskers or body hair.

The culture time in the culture method for hair follicular dermal sheath cells of the present invention is not particularly limited, and for example, the cells are continuously cultured or subcultured until the isolated hair follicular dermal sheath cells proliferate and increase by two times or more, preferably 10 times or more, more preferably 100 times or more.

Further, in the culture method for hair follicular dermal sheath precursor cells of the present invention, the precursor cells are cultured until the precursor cells differentiate into hair follicular dermal sheath cells, for example, for 500 hours or more, preferably 600 hours or more. Incidentally, the differentiation of the precursor cells into hair follicular dermal sheath cells can be confirmed by performing mixed transplantation of the cultured precursor cells and high-passage rat whisker-derived DP cells which lost a DS formation ability due to long-term subculture in combination in the dorsal area of a nude mouse, followed by observation of formation of the lower DS and DP, and so on.

EXAMPLES

Hereinafter, this invention will be described in more detail and specifically with reference to Examples, however, this invention is not limited to the following examples.

1. Method
1-1. Isolation of Hair Follicular Dermal Sheath (DS) and Dermal Papilla (DP)
1-1-1. Adult Rat Whiskers Male Wistar rat at 6 weeks of age was sacrificed under deep diethyl ether anesthesia, and cheek skins were collected such that the complete hair bulb was contained therein. The collected skins of rat cheek area were disinfected with Isodine (Meiji Seiyaku Co., Ltd.) and 70% ethanol, and then washed with cool Dulbecco's modified phosphate buffered saline (PBS(−)). From the washed skin, the hair follicles were collected. The collected hair follicle was cut above and below at one-half upper than the arrector pili muscle attachment site of the hair follicle (FIG. 1, cut was made at a position of the arrow A), and the respective portions were stored at 4° C. in 10% fetal bovine serum-containing Dulbecco's modified Eagle medium supplemented with 4.76 g/l of HEPES and 0.84 g of NaHCO$_3$ and adjusted to pH 7.4 (DMEM10/HEPES) until the subsequent step. Thereafter, (1) the lower DSs and DPs were isolated from the lower one-half of the hair follicles, and (2) the upper DSs were isolated from the upper one-half thereof.

(1) The lower DSs and DPs were isolated from the lower one-half of the hair follicles by cutting the hair bulbs. By using ophthalmic microsurgical knife and microforceps, the DSs and DPs in the hair bulbs were separated as one block from epidermal components such as the collagenous sheath and hair matrix. DSs and DPs were separated using a microsurgical knife at a connecting region located at the lowest end of the hair bulb (FIG. 1, cut was made at a position of the arrow B).

(2) The upper one-half of the hair follicle was treated with (DMEM10/HEPES) containing 1000 units/ml of Dispase (Sankyo Pharmaceutical Co., Ltd.) at 37° C. for 10 minutes, and after the Dispase treatment, it was washed well with DMEM10/HEPES. The upper DSs of the hair follicles were isolated using microforceps.

1-1-2. Human Scalp Hairs

Upon receiving the offer of the skin from an occipital hairy region of healthy male volunteers at the age of 34 and 46, the skin was collected. The collected scalp skins of the volunteers were divided along the direction of the hair follicles. Further, the skins were divided into a blocks containing skin and subcutaneous tissue for each hair follicular unit (FU) using a surgical knife. The resulting FU blocks were treated with (DMEM10/HEPES) containing 1,000 units/ml of Dispase at 37° C. for 10 minutes, and after the dispase treatment, it washed well with DMEM10/HEPES, FU, the skin, and subcutaneous tissue were separated from one another, and stored in DMEM10/HEPES at 4° C. until use. Thereafter, in the same manner in 1-1-1. rat whiskers, the lower DSs and DPs were isolated from the lower one-half of the hair follicle and the upper DSs were isolated from the upper one-half thereof.

1-2. Culture of DS Cells and DP Cells Derived from Rat Whiskers And Human Scalp Hair
1-2-1. Primary Culture and Subculture The isolated hair bulb DSs, upper DSs and DPs derived from human volunteer scalp were inoculated into a PRIMARIA 24-well cell culture plate (Becton Dickinson) for each tissue. The human hair bulb DS cells and DP cells were subjected to primary culture for 2 weeks using 5 types of culture media (Table 1) employing DMEM10 as a basal culture medium, and culture medium replacement was carried out every 4 days. As FGF2 (UPSTATE) and PDGF-AA (R&D SYSTEMS), human recombinants were used. After the primary culture, subculture was carried out every 7 days.

TABLE 1

Culture medium used in DS and DP cell culture

| | | | | | |
|---|---|---|---|---|---|
| Basal culture medium | 10% fetal bovine serum-containing Dulbecco's modified Eagle medium (DMEM10) | | | | |
| Culture medium name | DMEM10 | CM5 | FGF2 | PDGF-AA | PDGF-AA/FGF2 |
| Culture additive | No additives | Supernatant of rat plantar epidermal cell culture (50% v/v) | FGF2 (5 ng/ml) | PDGF-AA (10 ng/ml) | PDGF-AA (10 ng/ml) FGF2 (5 ng/ml) |

The upper DSs of human hair follicles were subjected to primary culture for 3 weeks with DMEM10 and DMEM10 supplemented with PDGF-AA/FGF2, respectively, and culture medium replacement was carried out every 4 days. On day 21 of the primary culture, cells were detached by an enzyme treatment, and the cell number was measured. After the primary culture, subculture was carried out every 7 days.

In the similar manner, the lower DSs, upper DSs and DPs derived from rat whiskers were seeded into a PRIMARIA 24-well cell culture plate for each tissue. The hair bulb DS cells and DP cells were subjected to primary culture for 2 weeks using 5 types of culture media (Table 1) employing DMEM10 as a basal culture medium, and culture medium replacement was carried out every 4 days. After the primary culture, subculture was carried out every 7 days. The upper DS of the hair follicle was subjected to primary culture for 2 weeks using DMEM10 supplemented with PDGF-AA/FGF2, and culture medium replacement was carried out every 4 days. On day 14 of the primary culture, cells were detached by an enzyme treatment, and the cell number was measured. After the primary culture, subculture was carried out every 7 days.

1-2-2. Measurement of Cell Proliferation Rate

On day 7 and day 14 after initiation of the primary culture, the cells cultured using each culture medium were washed with PBS(−) and fixed with 10% formalin. After the fixation, the cells were washed with physiological saline, and then, fluorescent nuclear staining with Hoechst was carried out. After nuclear staining was carried out, the whole cell colony was photographed with a digital camera (LEICA DC 500), and the digital image information was obtained, After this fluorescent image was converted to black and white, the number of cell nuclei was counted using Image J image analysis software. The cell proliferation was compared among the respective culture media. After the primary culture, subculture was carried out every 7 days. The culture medium replacement for cells was carried out every 4 days. A cell population doubling time (PDT) was calculated from the number of cells at each passage and comparison was made among the respective culture media. The number of proliferated cells under each condition was subjected to a statistical analysis using the Student t test.

1-2-3. Calculation of Total Number of Cells Capable of Proliferating by Culture The number of proliferated cells per one tissue at the time of finishing the primary culture is represented by (A). From the number of recovered cells during subculture at each passage (Harvest) and the number of inoculated cells at the start of culture (Initial), a multiple number of cell proliferation (Harvest/Initial) which indicates what multiple the cell number increased by is calculated. The resulting value is represented by (B). The value at the first passage is represented by ($B_1$). When all the cells obtained in the primary culture were subcultured and proliferated, a calculation method for the total number of cells obtained up to the first and third passages is as the following equations.

$$\text{The total number of cells obtained up to the first passage} = (A) \times (B_1)$$

$$\text{The total number of cells obtained up to the third passage} = (A) \times (B_1) \times (B_2) \times (B_3)$$

1-3. Assay for Function of DS Cells Derived from Human Scalp Hairs and Rat Whiskers

1-3-1. Preparation of Fibroblasts Derived from Adult Rat Sole Dermis

Male Wistar rats at 10-weeks-old were sacrificed under diethyl ether anesthesia, and the sole skins were excised. The excised sole skins were sterilized with Isodine and 70% ethanol and washed with PBS(−). Under a stereoscopic microscope, subcutaneous tissue attached to the sole skin was extracted using microscissors in a sterile atmosphere. After the extraction, the tissue was divided into quarters, and treated overnight at 4° C. in a dispase solution obtained by dissolving Dispase at 1,000 units/ml in DMEM10/HEPES. The skin tissue treated with Dispase was washed well with physiological saline, and the epidermis and the dermis were isolated. The resulting dermis was cut into pieces with a size of 1 to 2 square millimeters, which were explanted into a 60-mm culture dish, and primary culture of fibroblasts was carried out.

After the primary culture, the fibroblasts derived from the adult rat sole dermis were subcultured, and the cells up to the second to fourth passages were used for transplantation.

1-3-2. Preparation of Epidermal Cells of Newborn Rat

Epidermal cells having a hair growth and differentiation ability were prepared from the skin of a newborn Wistar rat at 2-days-old. The newborn Wistar rat was sacrificed under diethyl ether anesthesia, and the anterior and posterior limbs and tail were excised, and only the trunk region was obtained. The skin of the trunk region was peeled off and sterilized with Isodine and 70% ethanol. Then, the skin was washed with PBS(−), and stored at 4° C. until use. Under a stereoscopic microscope, subcutaneous tissue attached to the newborn rat skin was removed using microscissors in a sterile atmosphere. Incidentally, all the following processes were aseptically carried out in a clean bench or a sterile instrument.

The skin tissue was cut into strips with a width of about 3 mm and a length of about 10 mm, and treated overnight at 4° C. in a dispase solution obtained by dissolving Dispase at 1,000 units/ml in DMEM10/HEPES. The skin tissue treated with Dispase was washed well with cool PBS(−), and the epidermis and the dermis were isolated.

The isolated epidermis was cut into strips using a surgical knife and treated with 0.25% trypsin-EDTA solution at 37° C. for 10 minutes, whereby a nonadherent cell suspension was prepared. The resulting cell suspension was passed through filters with a mesh size of 100 μm and 40 μm, whereby aggregates in which a plurality of cells were adhered to one another were removed.

1-3-3. Preparation Method of Cell-Transplantation in DS Cell Function Assay In order to detect an ability to promote hair shaft elongation of the cultured DS cells, mixed transplantation of the cultured DS cells with rat whisker-derived DP cells (passage number: 39, p=39), which lost the dermal sheath formation ability due to long-term subculture was carried out, and an assay was carried out using hair shaft elongation promotion as an index. In the cell function assay, a chamber assay method (Non-patent document 2) in which adult rat whisker DP cells (passage number: 39), human lower DS cells from scalp hairs, rat upper DS cells from whisker hair follicles, newborn rat epidermal cells, fibroblasts derived from rat sole dermis were mixed according to a combination shown in Table 2, and the cells were transplanted in the dorsal area of a nude mouse was used. The cells to be transplanted were mixed according to each combination, centrifuged at 670 g for 5 minutes, whereby the cells were formed into a slurry. The culture medium was removed from the resulting pellet of cells for transplantation and the pellet was stored in the form of a slurry at 4° C. until transplantation.

TABLE 2

Cell conditions in cell function assay

| Transplanted cell name | New/passage number | Transplantation example 1 | Transplantation example 2 | Transplantation example 3 |
|---|---|---|---|---|
| Epidermal cells derived from newborn rat | Fresh | $1 \times 10^6$ | $1 \times 10^6$ | $2 \times 10^6$ |
| DP cells derived from adult rat whiskers | 39 | $3 \times 10^5$ | $3 \times 10^5$ | $6 \times 10^5$ |
| Fibroblasts derived from adult rat plantar dermis | 3 | $7 \times 10^6$ | $4 \times 10^5$ | $1.4 \times 10^6$ |
| Lower DS cells derived from human head hair follicles | 1 | — | $3 \times 10^5$ | — |
| Upper DS cells derived from adult rat whiskers | 39 | — | — | $6 \times 10^5$ |

1-3-4. Method for Cell Transplantation in DS Cell Function Assay

Male nude mice (available from Charles River Laboratories) at 4-weeks-old were anesthetized by intraperitoneal administration of PBS(−) containing 10% Somnopentyl (Kyoritsu Seiyaku Corporation) and 8% ethanol, and were placed in spontaneous lateral recumbency on a sterile drape. The entire trunk region of each mouse was disinfected with surgical Isodine (Meiji Seiyaku Co., Ltd.) and 70% ethanol, and all layers of the skin of the flank region thereof in the form of a circle with a diameter of 7 mm was excised and removed. In this region, a graft chamber having a dome portion with a diameter of 11 mm was inserted, a hat portion was inserted into the subcutaneous tissue, and the hat portion and the skin were sutured and fixed with a 5-0 nylon suture thread. In the transplanted area, the cell pellet was injected with a micropipette. All the processes up to the transplantation were aseptically carried out in a clean bench.

At one week after the cell transplantation, the graft chamber was removed, and isolation rearing of the mice was carried out for an additional 2 weeks while paying attention to infectious diseases and the contact behavior to the transplanted area by the mouse.

1-3-5. Method for Wait-And-See Approach (Macroscopic Observation of Hair Growth) and Histological Observation in DS Cell Function Assay At 3 weeks after the cell transplantation, the transplanted area was observed under a stereoscopic microscope (Leica), and the status of hair growth was photographed. After photographing, the transplanted area was extracted and fixed with Mildform 10 N (Wako Pure Chemical Industries) for one day and night at room temperature. Thereafter, paraffin embedding was carried out according to a common procedure, and serial tissue sections with a thickness of 5 μm were prepared. The tissue sections were subjected to hematoxylin-eosin (HE) staining and immunostaining using an anti-human smooth muscle-α-actin antibody (available from SIGMA) which is a marker for the hair follicular dermal sheath.

2. Results and Discussion 2-1. Primary Culture and Subculture of Lower DS Cells Isolated from Hair Bulb 2-1-1. Rat Lower DS Cells Derived from Whisker From the hair bulb of the rat whisker hair follicle, DSs and DPs were isolated (FIG. 1), and primary culture was carried out under the culture condition of the method 1-2. On 3 to 5 days after initiation of the primary culture, the tissues were attached on the culture dish, and cell colony formation and cell proliferation and migration were observed. The number of proliferated cells under each culture condition in two-week primary culture was counted by an image analysis. As a result, the number of proliferated cells of the rat-derived lower DS cells using PDGF-AA/FGF2 was about 8.5 times greater than that of the case of DMEM10 which is a conventional culture medium (*$p<0.05$, FIG. 2A). In a similar manner, in comparison with the case of DMEM10, the number of propagated cells in the case of CM5 (about 6.1 times greater than that of the case of DMEM10) and a culture medium with a single addition of FGF2 (about 4.3 times greater than that of the case of DMEM10) showed a higher value. Further, the case of PDGF-AA/FGF2 showed the highest value among the compared culture medium conditions (*$p<0.05$ vs. CM5: **$p<0.01$ vs. FGF2).

Figure 2:
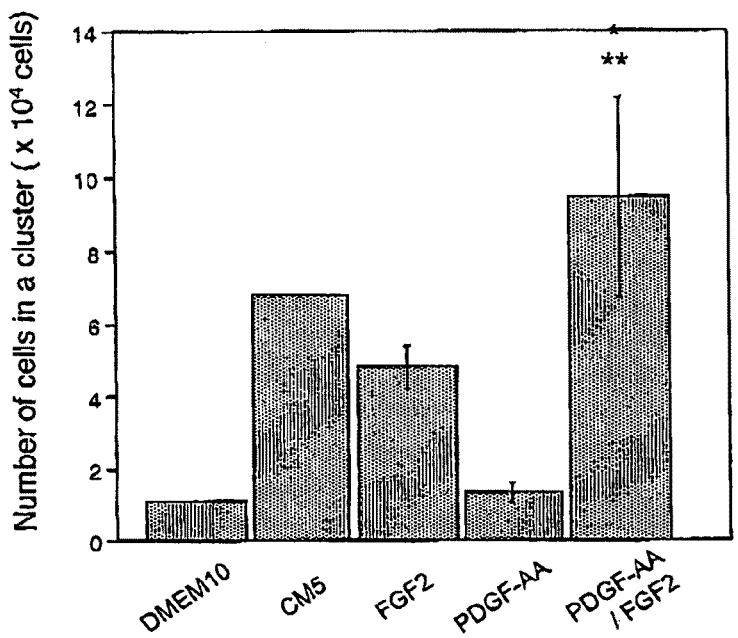
FIG. 2 shows the results of primary culture and subculture of rat whisker-derived lower DS cells. The lower DSs was isolated from the hair bulb of the rat whisker hair follicles and primary culture were carried out using a culture medium shown in Table 1. The number of cells which were attached to a plastic culture dish, formed a colonies, and migrated and propagated was counted by an image analysis. (A) The rat lDS cells which were propagated by the primary culture for 14 days using PDGF-AA/FGF2 showed a value about 8.5 times higher than that of the case of DMEM10. Similarly, even when comparison was made with the case of using CM5, a culture medium with a single addition of FGF2 or PDGF-AA, PDGF-AA/FGF2 showed the highest value. It was confirmed that in the primary culture, the number of propagated cells using PDGF-AA/FGF2 is significantly higher than that of the case of using a culture medium with a single addition of PDGF-AA or FGF2 growth factor (*p<0.05 vs. DMEM10, CM5: **p<0.01 vs. FGF2). (B) The lower DS cells subjected to primary culture using PDGF-AA/FGF2 were subcultured for 14 days. Subculture was carried out every 7 days, an average cell population doubling time (PDT) during the subculture was calculated, and comparison was made with the case of DMEM10.
Figure 2:
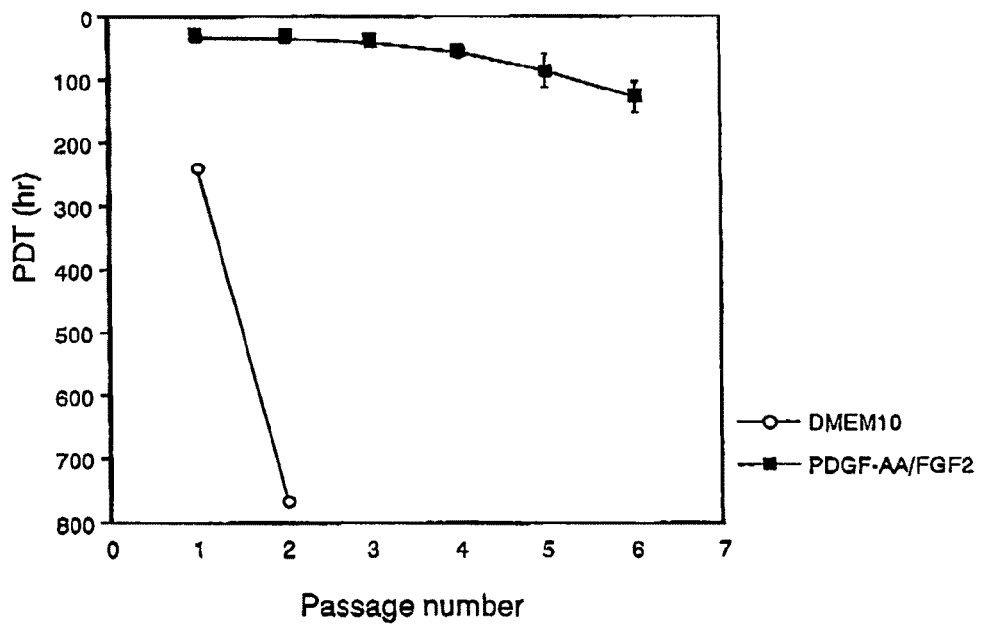

Further, after the primary culture, subculture was carried out every 7 days using the culture medium containing PDGF-AA/FGF2 which showed a high proliferation activity. A cell population doubling time (PDT) was calculated from the cell number at each passage, and comparison was made with the respective culture media (FIG. 2B). As a result, it was confirmed that also in the subculture, a significantly higher proliferation activity was shown in a culture medium supplemented with PDGF-AA/FGF2 than in a basal culture medium DMEM10.

2-1-2. Lower DS Cells of Hair Follicle of Human Scalp Hair

Since it was confirmed that rat-derived lower DS cells are effectively propagated with the culture medium containing PDGF-AA/FGF2, applicability thereof to human cells which have a high utility value was subsequently examined. Human cells have an extremely high utility value in medical application and development of pharmaceuticals. However, unless the cells can be proliferated to a sufficient number for each derived individual, the utility value thereof will decrease. Further, the provision frequency and amount of derived tissue are both minimized, therefore, it is important to minimize the risk of contamination by fungi, bacteria, etc. In primary culture, cells are acclimated over several weeks in the same culture dish, therefore, it is a step in which the risk of contamination is extremely high. Therefore, it is preferred that the culture medium condition provides a high cell proliferation rate in primary culture. Accordingly, the lower DS and DP (FIG. 1) were isolated from the hair bulb of human hair follicle, primary culture was carried out under the culture condition of the method 1-2, and comparison was made among the respective culture medium conditions as to cell proliferation rate in primary culture and the number of cells obtained in subculture.

Up to 3 to 7 days after initiation of the primary culture, the lower DS and DP tissues were attached on the plastic culture dish, and thereafter, colony formation of the attached cells and cell proliferation and migration were observed. In the primary culture separately performed twice using samples from the head hair of two volunteers, the success rate of tissue attachment using DMEM10 and CM5 was 50% or more and 90% or less. On the other hand, the success rate of tissue attachment in the case of PDGF-AA/FGF2 was 90% or more. Further, in the case of PDGF-AA/FGF2, the proliferation and migration of the attached cell colonies were observed earliest. In the case of human DP used as a control, 80% or more of the tissue was attached and colony formation was observed in every medium.

Figure 3:
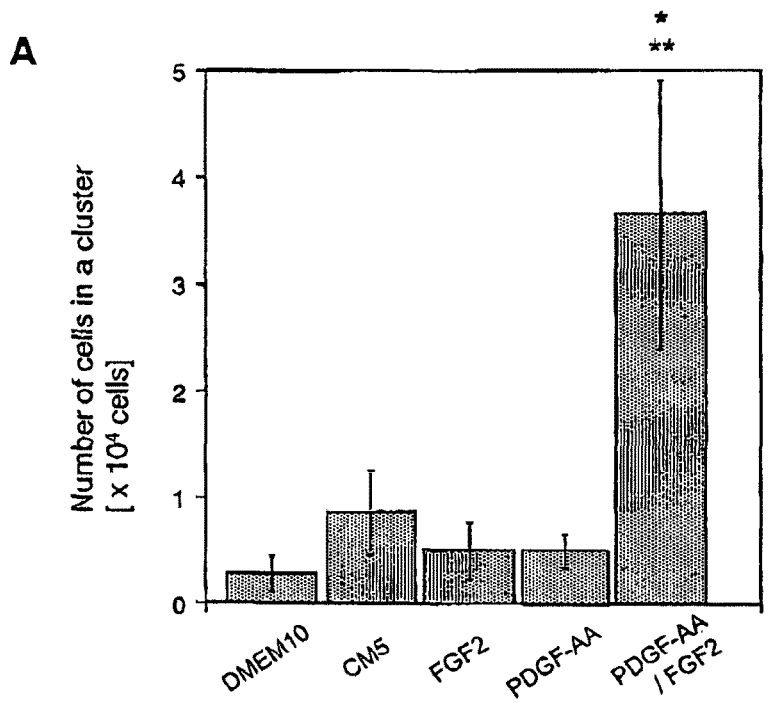
FIG. 3 shows the results of primary culture and subculture of human scalp hair-derived lower DS cells. The lower DSs were isolated from the hair follicle of human scalp hairs and primary culture were carried out under a culture medium condition shown in Table 1. The primary culture was carried out twice using the scalp hairs of each of two different volunteers separately. As a result, the success rates of attachment and colony formation of human lower DS were 50% or more and 90% or less in the case of DMEM10 and CM5. On the other hand, they were 90% or more in the case of PDGF-AA/FGF2. Further, in the case of PDGF-AA/FGF2, cell migration and proliferation after attachment was observed earliest. (A) The number of cells which formed a colony, and migrated and proliferated under each culture condition was counted by an image analysis. As a result, the number of proliferated cells of human lower DS using PDGF-AA/FGF2 was about 14 times greater than that of the case of DMEM10 (*p<0.05). Further, when comparison was made with the number of proliferated cells under a culture medium condition of CM5 (3.1 times greater than that of the case of DMEM10), a single addition of FGF2 (1.8 times greater than that of the case of DMEM10) or PDGF-AA (1.9 times greater than that of the case of DMEM10), the case of PDGF-AA/FGF2 showed a higher value than any other cases. These results showed that the proliferation activity in the case of PDGF-AA/FGF2 was significantly higher than that of the case of a single addition of PDGF-AA or FGF2 (**p<0.01 vs. CM5: *p<0.05 vs. FGF2, PDGF-AA). (B) The human lower DS cells subjected to primary culture using PDGF-AA/FGF2 were subcultured under the same culture medium condition, and an average cell population doubling time (PDT) at each passage was measured. In subculture using PDGF-AA/FGF2, a PDT of about 40 hours was maintained until the third passage, however, the PDT increased in a passage number-dependent manner thereafter.
Figure 3:
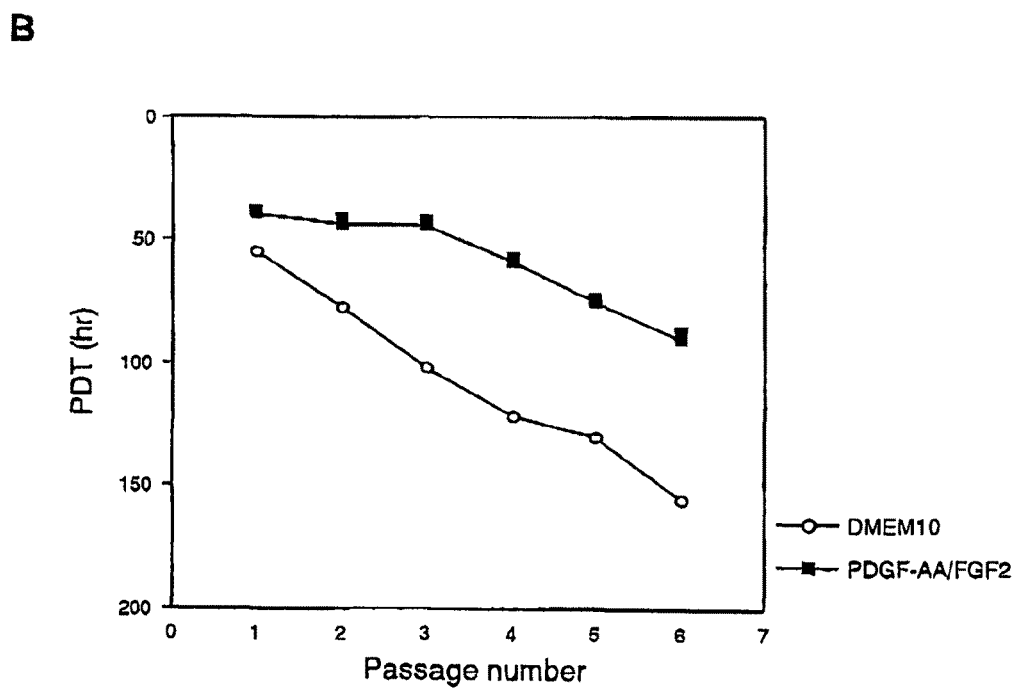

Two-week primary culture was carried out under each culture condition, and the number of cells which formed a colony and proliferated was counted by an image analysis (FIG. 3A). As a result, the number of proliferated cells of human DS cells using PDGF-AA/FGF2 was about 14 times greater than that of the case of DMEM10 (FIG. 3A, $*p<0.05$). When comparison was made with the case of a basal culture medium, DMEM10, any of CM5 (about 3.1 times greater than that of the case of DMEM10) and a culture medium with a single addition of FGF2 (about 1.8 times greater than that of the case of DMEM10) or PDGF-AA (about 1.9 times greater than that of the case of DMEM10) showed high cell proliferation, however, it was significantly lower than that of the case of PDGF-AA/FGF2 (FIG. 3A). Further, by a statistical analysis, it was confirmed that PDGF-AA/FGF2 shows a significantly higher cell proliferation activity than the conditions of a single addition of FGF2 and PDGF-AA (FIG. 3A, $**p<0.01$ vs. CM5: $*p<0.05$ vs. FGF2, PDGF-AA).

Figure 4:
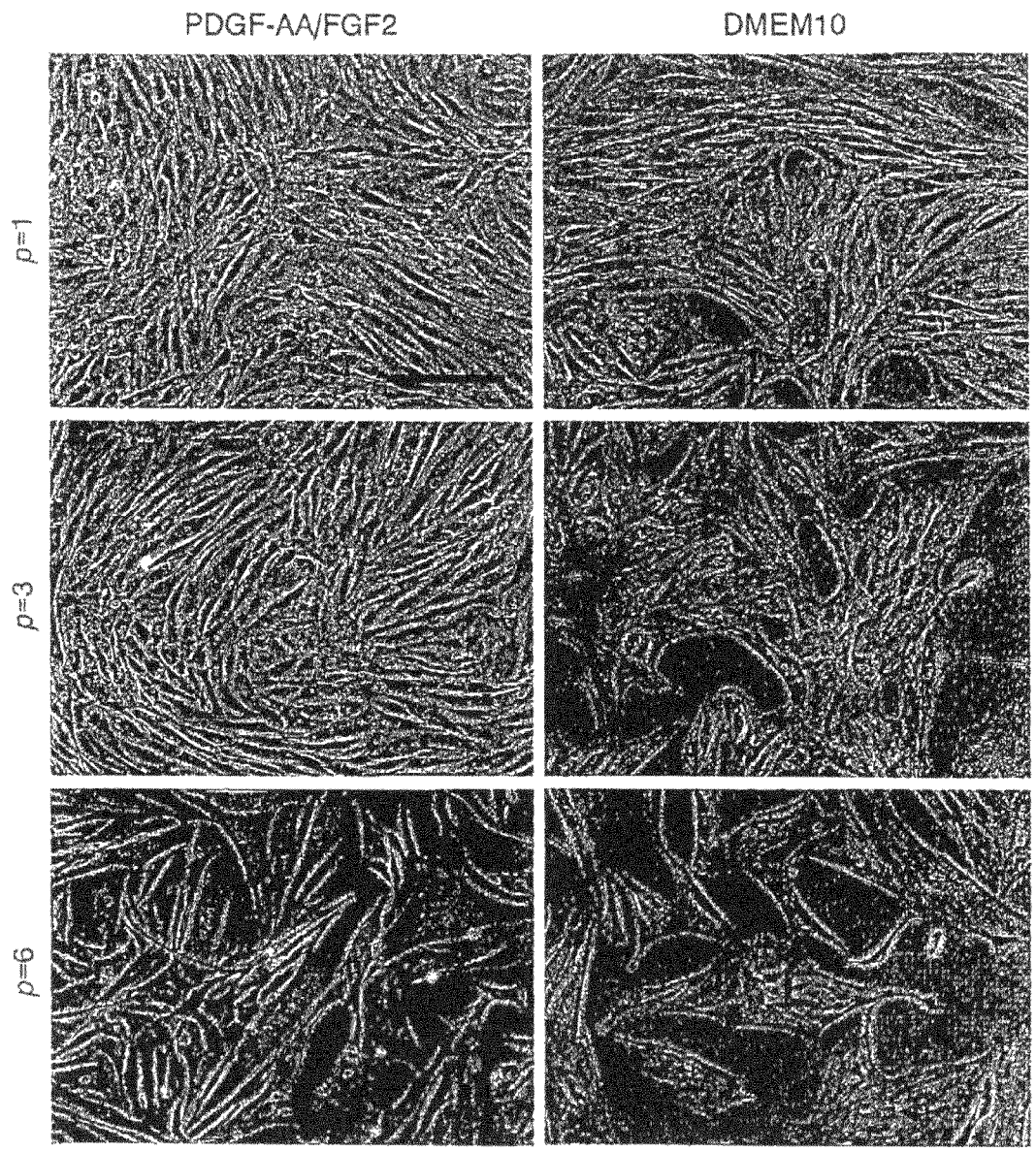
FIG. 4 shows microscopic images of primary culture and subculture of human scalp air-derived lower DS cells. As a result, the cell morphology of a small spindle shape was maintained from the first passage to the third passage in the case of PDGF-AA/FGF2, however, thereafter, the cell morphology gradually changed into a flat shape accompanying stress fiber formation, which shows cell aging (PDGF-AA/FGF2). On the other hand, in the case of DMEM10, the cells already took a flat shape with stress fibers in the first passage (DMEM10), therefore, the effectiveness of PDGF-AA/FGF2 was shown also in the cell morphology. Bar: 200 μm

Subsequently, the lower DS cells subjected to primary culture under the respective culture medium conditions of PDGF-AA/FGF2 and DMEM10 were subcultured (7 days/passage) under the same culture medium condition, and comparison was made among the respective culture medium conditions as to an average cell population doubling time (PDT) at each passage. As a result, the case of PDGF-AA/FGF2 showed a higher proliferation rate than the case of DMEM10 in all the passages measured. However, the proliferation rate after the third passage was gradually lowered even in the case of PDGF-AA/FGF2 (FIG. 3B). Further, in the case of PDGF-AA/FGF2, the cells maintained a cell morphology of a small spindle cell shape from the first passage to the third passage, however, thereafter, a flat shape accompanying stress fiber formation, which is a sign showing cell aging, gradually came to be observed (FIG. 4, p=6, PDGF-AA/FGF2). On the other hand, in the case of DMEM10, the cells took a flat shape with stress fibers from the first passage (p=1) (FIG. 4, DMEM10), therefore, the effectiveness of PDGF-AA/FGF2 was shown also in the cell morphology.

In the regenerative medicine and development of pharmaceuticals, it is important to stably obtain a large amount of normal cells in a short time. Accordingly, the maximum number of cells obtained up to the third passage until which the stable proliferation rate and cell morphology can be maintained was calculated by the method described in the method 1-2. As a result, the maximum cell number in the case of PDGF-AA/FGF2 was 450 times greater than that of the case of DMEM10 (Table 3). These results showed that PDGF-AA/FGF2 culture medium can culture and proliferate the lower DS cells derived from the hair bulb of human scalp hair in a shorter time than a conventional method (DMEM10), and can secure a cell number which can be sufficiently applied to a treatment or development of pharmaceuticals.

Incidentally, in the subculture after the first passage in Table 3, the cells were inoculated at a cell density of $6.6 \times 10^4$ cells/$\phi$6 cm dish. On day 4, the total volume of the culture medium was replaced, and subculture was carried out on day 7. From the number of cells recovered at each passage, the total number of cells obtained up to the third passage was calculated using the method of 1-2. When the value in the case of DMEM10 was taken as 1 and comparison was made, the total number of cells obtained up to the third passage was 450 times and the superiority of PDGF-AA/FGF2 is shown.

TABLE 3

Comparison between culture medium conditions as to primary culture and subculture of human head hair-derived lower DS cells and maximum number of proliferated cells

| Passage number/culture (days) | | Culture medium condition | |
|---|---|---|---|
| | | DMEM10 | PDGF-AA/FGF2 |
| | | Cell number ($\times 10^3$ cells) | |
| Primary culture | 14 | 2.8 | 36.6 |
| Passage number 1 | 7 | 542.5 | 1220.0 |
| 2 | 7 | 330.0 | 1150.0 |
| 3 | 7 | 208.0 | 891.0 |
| Comparison of the total number of cells obtained up to the third passage (Relative value when taking the value in the case of DMEM10 as 1.0) | | 1.0 | 445.0 |

2-2. Analysis for Function of Lower DS Cells

Rat whisker-derived DP cells proliferated by long-term subculture using the method described in Patent document 2 sustain an ability to induce hair follicle formation, but an ability to grow hair shafts from the hair follicles whose formation has been induced is reduced and lost (Patent document 1). As a method for solving this problem, the present inventors found that by adding a given amount of DS cells to DP cells whose ability to grow hair shafts has been reduced due to long-term subculture, the reduced ability to induce hair growth is restored and the growth of hair emerging from the hair follicle is significantly promoted (Patent document 1). In order to confirm that the lower DS cells cultured using PDGF-AA/FGF2 of the present invention maintain this function, the following study was carried out.

Figure 5:
FIG. 5 shows the results of an analysis for function of human scalp hair-derived lower DS cells. A cell transplantation study for confirming the function of DS cells of the hair bulbs cultured using a PDGF-AA/FGF2-containing culture medium was carried out. DS cells of the hair bulb of the human scalp hair follicle were combined with high-passage rat whisker DP cells, which lost a DS formation ability due to long-term subculture (Table 2), and the mixed cells were transplanted in the dorsal area of a nude mouse. At 4 weeks after the transplantation, the status of hair growth in the area transplanted with cells (in the dashed line circle) was photographed, and a biopsy was carried out. A biopsy tissue was subjected to formalin fixation and paraffin embedding, and serial tissue sections with a thickness of 5 μm were prepared. Then, the tissue sections were subjected to HE staining and immunostaining using an anti-α-SMA antibody. (A) In the group of single transplantation with high-passaged rat DP cells (p=40), the skin (in the dashed line circle) was formed by cell transplantation, however, hair growth was not observed. (B) As a result of histological observation of the group of single transplantation with high-passaged rat DP cells, incomplete hair follicles (dashed line area) in which a hair shaft was not formed were observed (H&E staining). (C) In these hair follicles, DS which is positive to anti-α-SMA antibody was not observed. Vascular endothelial cells are positive to anti-α-SMA antibody, however, they have a luminal structure and include blood cells therein, therefore, they can be clearly distinguished from DS (arrows).
Figure 5:
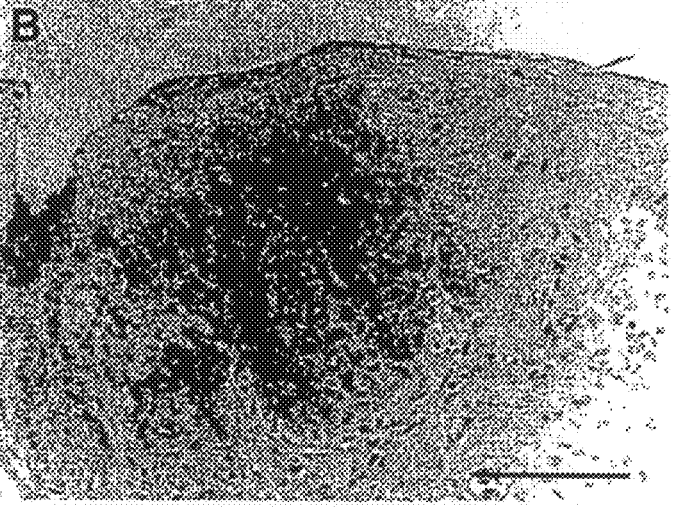
Figure 5:
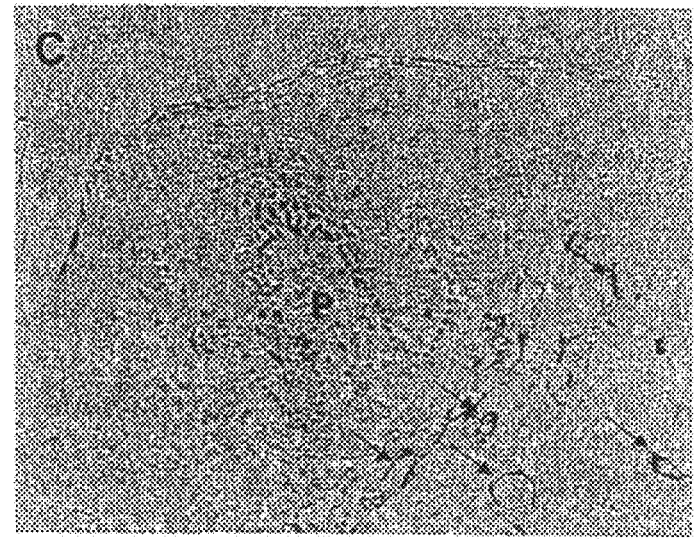
Figure 6:
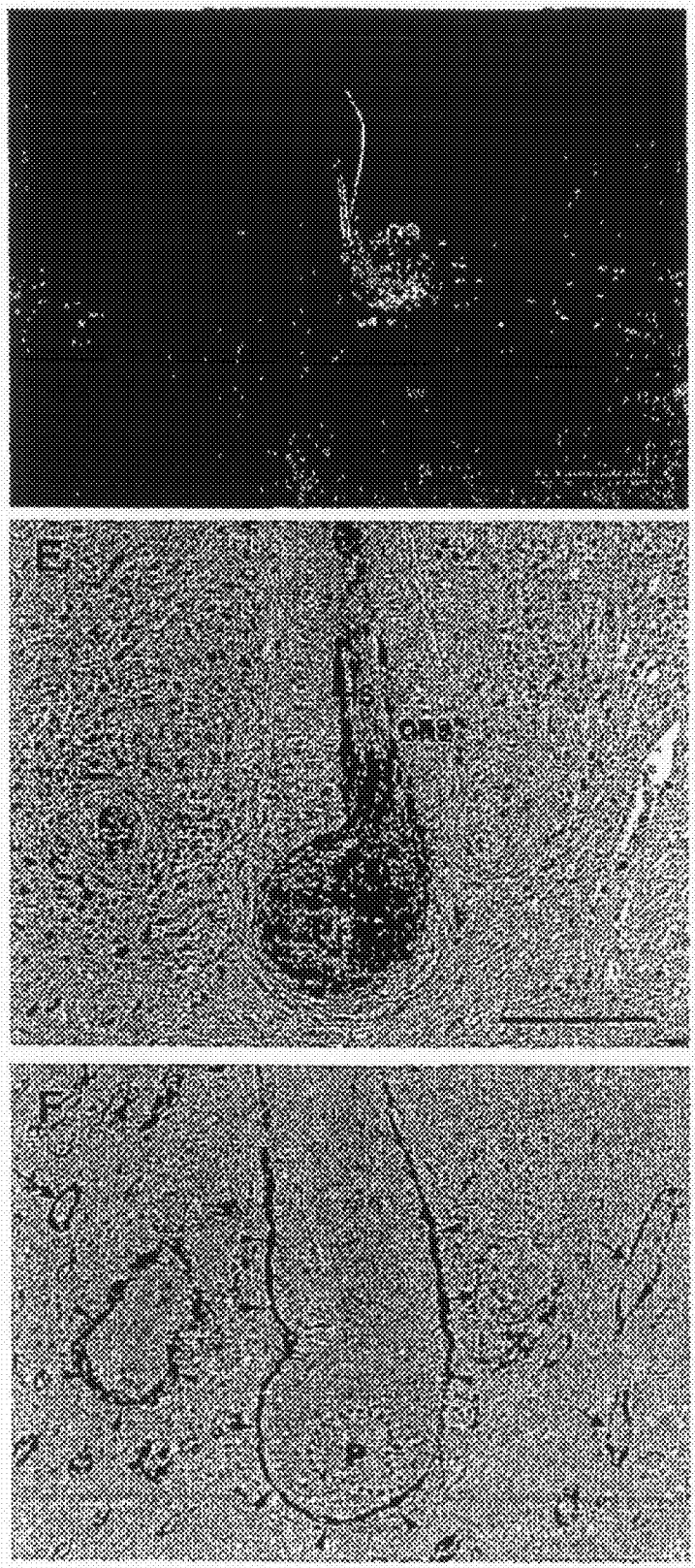
FIG. 6 shows the results of an analysis for function of human scalp hair-derived lower DS cells under the same condition as in FIG. 5. (D) In the experimental group in which transplantation was carried out by adding human DS cells (p=1) to the high-passaged rat DP cells (p=40), hair growth (in the dashed line circle) was apparently observed. (E) The tissue in the dashed line in the macrophotograph (C) was subjected to a biopsy, and observation by H&E staining was carried out. As a result, in the group with the addition of human scalp hair-derived lower DS cells, a lot of hair follicles accompanying hair shaft formation were observed. (F) Further, a layer of cells which are positive to anti-α-SMA antibody was observed in the outermost layer of the hair follicle (arrows). The arrows indicate vascular endothelial cells. HM; hair matrix; ORS: outer root sheath; HS: hair shaft; P: dermal papilla; Bars in A and D: 1 mm; in B and E: 100 μm
Figure 7:
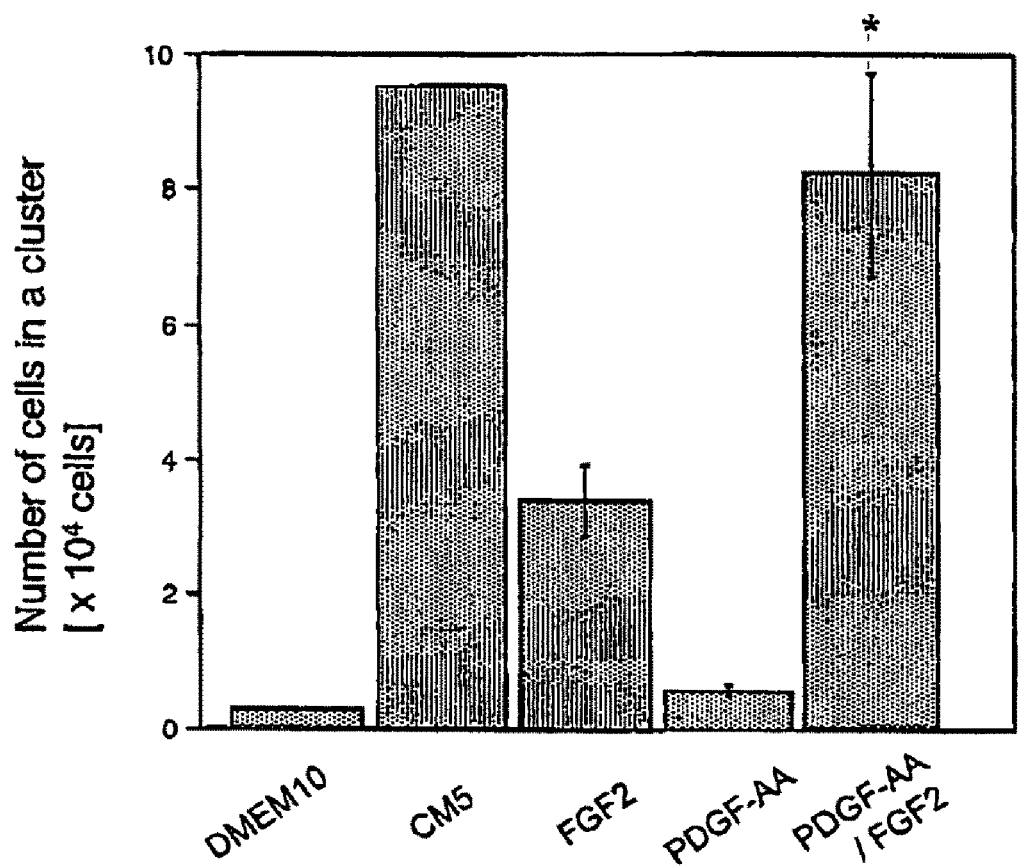
FIG. 7 shows the results of primary culture of rat whisker-derived DP cells. DPs were isolated from the hair bulbs of the rat whiskers and subjected to primary culture for 2 weeks using a culture medium described in Table 1. The number of cells which formed a colony and migrated and proliferated under each culture condition was counted by an image analysis. As a result, PDGF-AA/FGF2 showed a proliferation activity equivalent to that of the case of DP cell growth medium (CM5) described in a prior patent (Patent document 2) and showed a higher proliferation activity than that of the case of a single addition of FGF2 or PDGF-AA.

Mixed transplantation of the human scalp hair-derived lower DS cells (p=1) and high-passage rat whisker DP cells (p=39) which lost a DS formation ability due to long-term subculture in combination was carried out, and restoration of ability to grow hair shafts and the presence or absence of DS formation in the hair follicle whose formation has been induced were examined (Table 2, Transplantation example 2). As a result, in the group of transplantation with high-passaged rat DP cells, apparent hair growth was not observed (FIG. 5-A), however, in the group with the addition of human DS cells cultured using PDGF-AA/FGF2, the ability to grow hair was apparently restored (FIG. 6-ID). In the histological observation (H&E) of the cell transplantation site, a lot of hair follicles which formed hair shafts were observed in the group with the addition of the human scalp hair-derived lower DS cells (FIG. 6-E), however, in the group of single transplantation with rat whisker DP cells, incomplete hair follicles which do not form hair shafts were observed (FIG. 5-B). Further, when the same serial tissue sections were subjected to immunostaining with an anti-α-SMA antibody, a layer of cells which are positive to α-SMA was observed in the outermost layer of the hair follicle in the group with the addition of the human scalp hair-derived lower DS cells (FIG. 6-F). On the other hand, in the group with no addition, a layer of cells which are positive to α-SMA was not observed in the outermost layer of the hair follicle (FIG. 5-C).

From the above results, it was demonstrated that by using PDGF-AA/FGF2 of the present invention, the lower DS cells can be cultured and propagated while sustaining their function.

2-3. Primary Culture and Subculture of DP Cells Using PDGF-AA/FGF2

DS cells include precursor cells of DP cells, and DP cells differentiated from DS cells and proliferated are supplied to the dermal papilla from the lowest end of the hair bulb by way of the papillary stalk. Also, they are histologically connected at the lowest end of the hair bulb at the papillary stalk, and when DSs and DPs are isolated from hair follicles, they are collected as one block. The present inventors have made it possible by adding a given amount of hair follicular dermal sheath cells to dermal papilla cells whose ability to grow hair shafts has been reduced due to long-term subculture, to restore the reduced ability to induce hair growth and to significantly promote the growth of hair shafts emerging from the hair follicle and already have applied for patent (Patent document 1). Accordingly, if DS cells and DP cells which are close in terms of cell differentiation and structure can be cultured under the same condition, the method can have an extremely high utility value.

Accordingly, it was verified that the PDGF-AA/FGF2 culture medium can be used for culture of rat whisker-derived DP cells. As a result, PDGF-AA/FGF2 culture medium showed a significantly higher proliferation activity than DMEM10 (FIG. 5, *$p<0.001$ vs. DMEM10). It showed a proliferation activity equivalent to that of the case of DP cell growth medium (CM5) (Non-patent document 1, Patent document, 2) which has been previously applied for patent.

Figure 8:
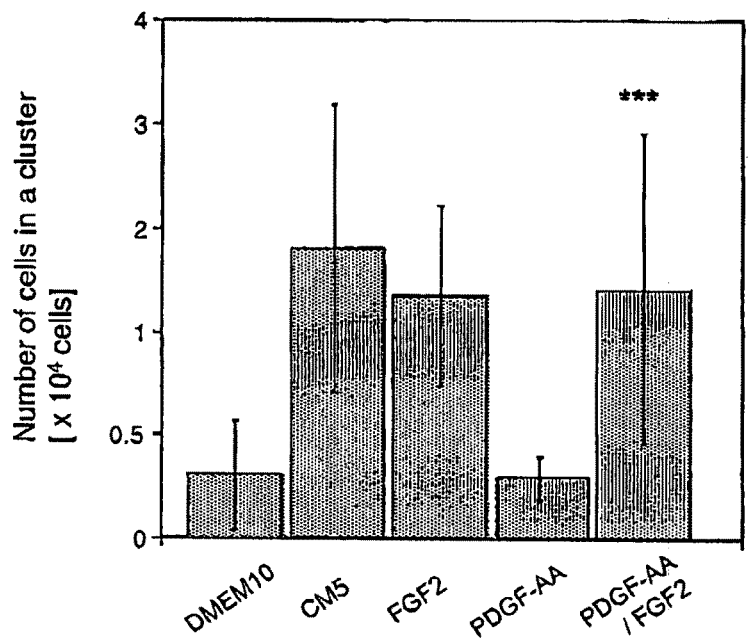
FIG. 8 shows the results of primary culture and subculture of human scalp hair-derived DP cells. The lower DP was isolated from the hair follicle of normal scalp provided from a male volunteer, and subjected to primary culture for 14 days under a culture medium condition described in Table 1. The number of proliferated cells which were attached and formed a colonies were counted by image processing, and comparison was made as to the number of proliferated cells per one DP. (A) PDGF-AA/FGF2 showed a high proliferation activity equivalent to that of the case of CM5. Further, it was shown that the proliferation activity was significantly higher even when comparison was made with the case of DMEM10, FGF2 or PDGF-AA (***p<0.05 vs. DMEM10, FGF2 or PDGF-AA). (B) The human DP cells subjected to primary culture were subcultured every 7 days, and comparison was made among the respective culture medium conditions as to an average cell population doubling time (PDT) at each passage. As a result, PDGF-AA/FGF2 showed a higher proliferation activity than that of the case of DMEM10 in all the passages up to the fourth passage. However, there was a tendency that the PDT value gradually increases in a passage number-dependent manner in the subculture using PDGF-AA/FGF2. On the other hand, in the case of CM5, a tendency that the PDT value gradually decreases was observed.
Figure 8:
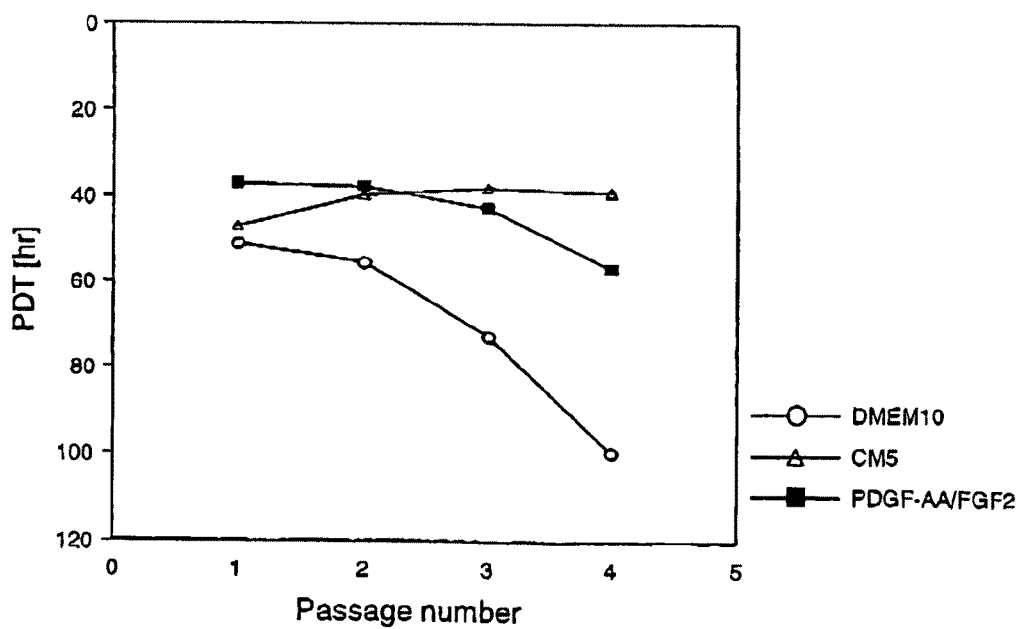

Subsequently, the effect of PDGF-AA/FGF2 on human scalp hair-derived DP cells which have a high utility value was verified. As a result, it was shown that in primary culture, the numbers of propagated cells using CM5 and PDGF-AA/FGF2 were equivalent to each other. Further, it was shown that PDGF-AA alone has an effect equivalent to that of the case of DMEM10, and a composition of PDGF-AA/FGF2 is effective in the same manner as CM5 (FIG. 8-A), Subsequently, rat DP cells subjected to primary culture under the respective culture medium conditions of PDGF-AA/FGF2, CM5 and DMEM10 were subcultured (7 days/passage) under the same culture medium condition, and comparison was made among the respective culture medium conditions as to an average cell population doubling time (PDT) at each passage (FIG. 8-5). As a result, PDGF-AA/FGF2 showed a higher proliferation rate than any other conditions up to the second passage, however, after the third passage, the PDT value increased and the proliferation rate was lower than that of the case of CM5 (FIG. 8-B). However, when comparison was made as to the maximum cell number of DP cells obtained up to the third passage until which the stable proliferation rate and cell morphology can be maintained, the maximum cell number in the case of PDGF-AA/FGF2 was 1.4 times greater than that of the case of CM5 (about 70 times greater than that of the case of DMEM10) (Table 4). It was confirmed that also for the human and rat DP cells, PDGF-AA/FGF2-containing culture medium has a high proliferation activity equivalent to that of the case of CM5, therefore, it was demonstrated that PDGF-AA/FGF2 is effective also in DP culture. This indicated that DS cells and DP cells can be simultaneously cultured under the same condition. Incidentally, in the subculture after the first passage in Table 4, the cells were seeded at a cell density of $6.6\times10^4$ cells/φ6 cm dish. On day 4, the total volume of the culture medium was replaced, and subculture was carried out on day 7. When comparison was made as to the total number of cells obtained up to the third passage based on the number of cells recovered at each passage up to the third passage using the method of 1-2 by taking the value in the case of DMEM10 as 1, it was 70 times, which was 1.4 times greater than that of the case of CM5. These results were different from those of human DS, however, the highest proliferation activity was observed in the PDGF-AA/FGF2-containing culture medium for both human DS/DP cells.

TABLE 4

Comparison among culture medium conditions as to primary culture and subculture of human head hair-derived DP cells and maximum number of proliferated cells

| Passage number/ Culture days (days) | | Culture medium condition | | |
|---|---|---|---|---|
| | | DMEM10 | CM5 | PDGF-AA/FGF2 |
| | | Cell number (×10³ cells) | | |
| Primary culture | 14 | 3.0 | 14.0 | 12.1 |
| Passage number | 1 | 7 | 645.0 | 782.5 | 1540.0 |
| | 2 | 7 | 540.0 | 124.0 | 1438.0 |
| | 3 | 7 | 293.0 | 1145.0 | 832.5 |
| Comparison of the total number of cells obtained up to the third passage (Relative value when taking the value in the case of DMEM10 as 1) | | 1.0 | 50.2 | 70.2 |

2-4. Primary Culture and Subculture of Upper DS Cells Using PDGF-AA/FGF2 Culture Medium In general, it is defined that DS is a tissue which surrounds the outer side of the hair follicle and is composed of anti-α-SMA antibody positive dermal cells. However, DS cells which are positive to anti-α-SMA antibody disappear in the telogen phase in hair cycle, therefore, the existence of precursor cells of DS cells has been postulated. The present inventors paid attention to a structure (referred to as upper DS) composed of dermal cells which surround the bulge region of the hair follicle in the anagen phase, are negative to anti-α-SMA antibody and positive to anti-vimentin antibody, and are structurally continuous with DS (referred to as lower DS for the sake of convenience) which is positive to anti-α-SMA antibody and distributed in the lower side of the bulge region (FIG. 1). If the upper DS cells are assumed to be precursor cells of the lower DS and DP cells, it is considered that cell transplantation is carried out in the same manner as in the assay for function of the lower DS cells, the lower DS and DP derived from the upper DS cells are formed. Accordingly, based on this assumption, it was verified that in the upper DS, precursor cells of the lower DS cells and DP cells are included. However, in this verification study, a large amount of upper DS cells are required, therefore, firstly, it was confirmed that the upper DS cells derived from rat whiskers and human scalp hair can be cultured in the same manner as the lower DS cells.

2-4-1. Rat Whisker-Derived Upper DS Cells

Figure 9:
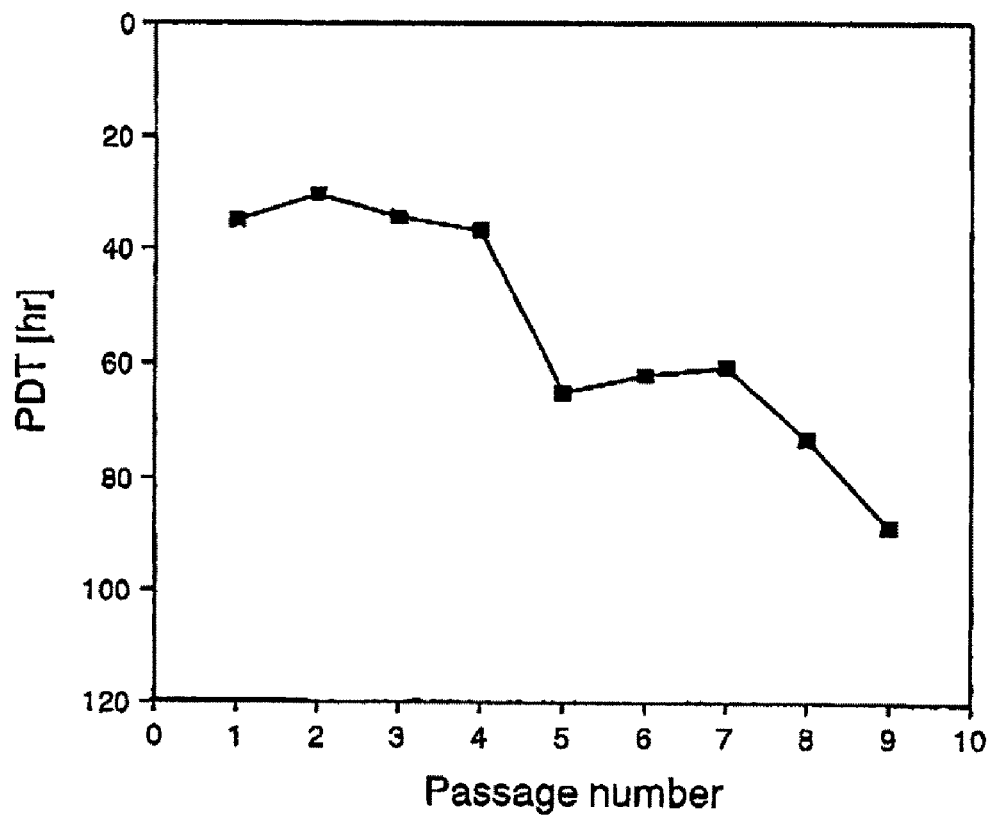
FIG. 9 shows the results of subculture of rat whisker-derived upper DS cells. The upper DSs were isolated from the rat whisker hair follicles, and cultured using DMEM10 or PDGF-AA/FGF2 culture medium. Although the proliferation rate of the upper DS was lower than that of the DS cells of the hair bulb and the primary culture took 21 days, the cells propagated by two times greater than that of the case of a basal culture medium, DMEM10. Further, when subculture was carried out, a high proliferation rate about 40 hours was sustaining until the fourth passage, however, thereafter, the PDT value increased.

The upper DSs were isolated from the rat whisker hair follicles by the method described in 1-1 and cultured in PDGF-AA/FGF2 culture medium which was effective in the culture of DS cells. Although the proliferation rate of the upper DS cells was lower than that of the lower DS cells of the hair bulb and the primary culture took 21 days, the number of proliferated cells was two times greater than that of the case of DMEM10. Further, when subculture was carried out, a high proliferation rate about 40 hours was maintained until the fourth passage, however, thereafter, the PDT value increased (FIG. 9).

2-4-2. Human Scalp Hair-Derived Upper DS Cells

The upper DS was isolated from the hair follicle of human scalp hair by the method described in 1-1 and subjected to primary culture and subculture using PDGF-AA/FGF2. In the primary culture, PDGF-AA/FGF2 showed a proliferation activity 2.2 times greater than that of the case of DMEM10 in the same manner as the results of the case of rat. Further, when the total number of cells obtained from the primary culture to the third passage was calculated by the calculation method described in the method 1-4, total number of cells in the case of PDGF-AA/FGF2 was about 2.2 times greater than that of the case of DMEM10 (Table 5). Incidentally, in the subculture after the first passage in Table 5, the cells were seeded at a cell density of $6.6 \times 10^4$ cells/φ6 cm dish. On day 4, the total volume of the culture medium was replaced, and subculture was carried out on day 7. From the number of cells recovered at each passage, the total number of cells obtained up to the first passage was obtained using the method of 1-2. When the value in the case of DMEM10 was taken as 1 and comparison was made, the total number of cells obtained up to the first passage was 2.2 times.

TABLE 5

Comparison between culture medium conditions as to primary culture and subculture of human head hair-derived upper DS cells and maximum number of proliferated cells

| Passage number/culture (days) | | Culture medium condition | |
|---|---|---|---|
| | | DMEM10 | PDGF-AA/FGF2 |
| | | Cell number ($\times 10^3$ cells) | |
| Primary culture | 21 | 1.5 | 2.2 |
| First passage | 7 | 8.1 | 18.0 |
| Comparison of the total number of cells obtained up to the first passage (Relative value when taking the value in the case of DMEM10 as 1) | | 1.0 | 2.2 |

From the above results, it was shown that the upper DS cells can be also effectively proliferated using PDGF-AA/FGF2.

Figure 10:
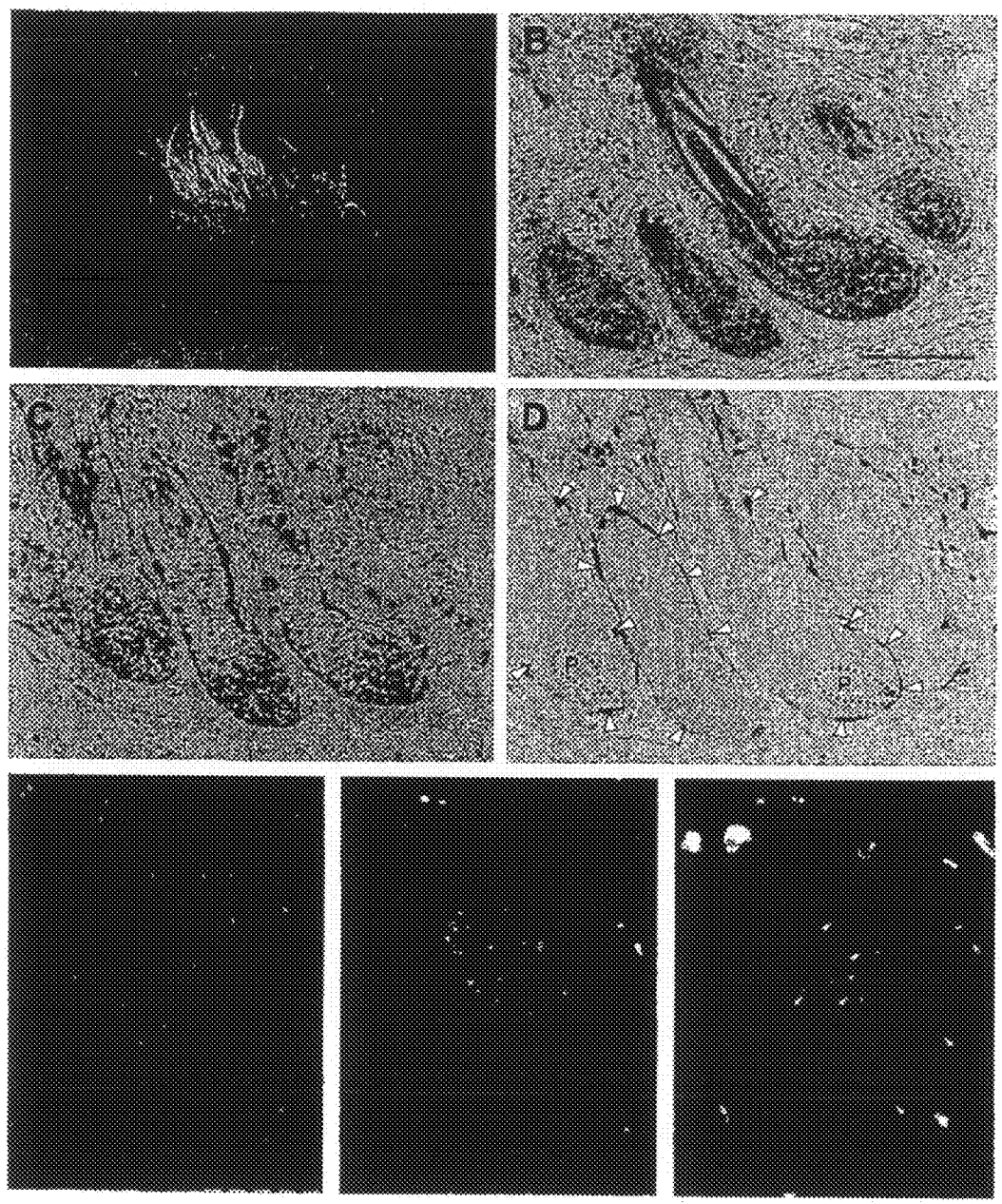
FIG. 10 shows the results of an analysis for function of rat whisker-derived upper DS cells. Rat upper DS cells were combined with high-passaged rat whisker DP cells, which lost a DS formation ability due to long-term subculture, and mixed transplantation in the dorsal area of a nude mice were carried out. At 3 weeks after the transplantation, the status of hair growth in the area transplanted with cells (in the dashed line circle) was photographed, and a biopsies were carried out. A biopsy tissues were subjected to formalin fixation and paraffin embedding, and serial tissue sections with a thickness of 5 μm were prepared. Then, the tissue sections were subjected to H&E staining and immunostaining using an anti-α-SMA antibody and anti-EGFP antibody. (A) A macrophotograph of a transplanted area (in the dashed line circle) in which an ability to grow hair was restored. It was shown that by the addition of the upper DS cells, an ability to grow hair was restored. (B) The transplanted area in which an ability to grow hair was restored was subjected to a biopsy, and a histological observation was carried out. A lot of hair follicles accompanying hair shaft formation were observed (H&E). (C) A DS layer composed of anti-α-SMA antibody-positive cells was observed in the outermost layer of these hair follicles (arrowheads). The arrows indicate vascular endothelial cells. (D) Further, when the added rat upper DS cells were tracked by immunostaining using anti-EGFP antibody, it was shown that the cells derived from the rat upper DS cells are distributed in DS and DP (arrowheads). (E to G) Further, when these hair follicles were observed in detail with a fluorescent microscope, cells expressing EGFP were observed in a part of DP. By Hoechst nuclear staining (E), the range of dermal papilla (dashed line; P: dermal papilla) was determined. In this DP region, upper DS-derived cells (G) with EGFP fluorescence were observed among the high-passage DP cells (F) labeled with DiI fluorescence. The arrows indicate red blood cells emitting fluorescence by G and B excitation. Bars in A: 1 mm; in B: 100 μm; and in E: 50 μm

2-5. Analysis for Function of Upper DS Cells Cultured Using PDGF-AA/FGF2 Culture Medium If the upper DS cells are assumed to be precursor cells of the lower DS and DP cells, when cell transplantation is carried out according to the method 1-3, the upper DS cells can differentiate into the lower DS and DP cells. Accordingly, it was verified that in the upper DS, precursor cells of the lower DS cells and DP cells are included. Mixed transplantation of high-passage rat DP cells and the upper DS cells derived from whiskers of an EGFP-transgenic (EGFP-Tg) rat cultured using PDGF-AA/FGF2 (Table 2, Transplantation example 3) was carried out, and an examination of restoration of an ability to grow hair and a histological analysis were carried out. As a result, while hair growth was not observed in the group of transplantation with high-passage DP cells (p=39) (FIG. 5-A), the restoration of hair growth was apparently observed in the group with the addition of the rat whisker-derived upper DS cells (p=1) (FIG. 10-A). Also in the histological observation, a lot of hair follicles that made hair shafts were observed in the group with the addition of the upper DS cells of the rat whisker hair follicle. Further, when the serial tissue sections were subjected to immunostaining with an anti-α-SMA antibody, which is a marker for DS, a layer of cells which are positive to anti-α-SMA antibody was observed in the outermost layer of the hair follicle in the group with the addition of the upper DS cells of the rat whisker hair follicle (FIG. 10-C). On the other hand, in the case of only the high-passaged DP cells, cells which are positive to anti-α-SMA antibody was not observed in the outermost layer of the hair follicle (FIG. 5-B). Further, because the transplanted DS cells were derived from the EGFP-Tg rat, serial sections of anti-α-SMA antibody-positive hair follicles were subjected to GFP fluorescence observation and anti-EGFP antibody immunostaining, and it was verified that they were derived from the transplanted upper DS cells. As a result, it was found that the lower DS of the hair follicle whose ability to grow hair shafts has been restored by the addition of the upper DS cells expressed EGFP (FIG. 10-D). In addition, EGFP-expressing cells were observed in a part of DP in the same experimental group (FIGS. 10-E, F, G).

The original tissue from which the upper DS cells used in the above study were derived is a tissue which is negative to anti-α-SMA antibody in vivo. It has been reported so far that from the results of a transplantation study of the hair follicle from which a specific site was removed (Non-patent documents 12 and 13) or a transplantation study of the upper DS cells cultured only with DMEM10 (Non-patent document 7), the upper DS cells do not differentiate into DP cells unlike the lower DS cells. Therefore, it has been believed so far that the upper DS does not include precursor cells of lower DS and DP cells. However, it was confirmed for the first time by the present invention that cultured rat whisker upper IDS cells differentiate into the lower DS and DP and have a function of restoring an ability to grow hair. This result indicated that the upper DS cells are precursor cells having an ability to differentiate into the lower DS and DP cells.

As described above, the present invention has made it possible not only to proliferate the lower DS cells while sustaining their function, but also to culture and propagated cells having a function equivalent to that of the lower DS cells using precursor cells contained in the upper DS. Further, it can be said that the culture method according to the present invention is a method for controlling the differentiation tendency of DS precursor cells with low differentiation which do not express a differentiation marker and proliferating them.

The invention claimed is:

1. A culture method for proliferating hair follicular dermal sheath cells while maintaining their function, which comprises culturing the hair follicular dermal sheath cells in an animal cell culture medium supplemented with platelet-derived growth factor AA (PDGF-AA) and fibroblast growth factor 2 (FGF2).

2. The culture method according to claim 1, wherein the hair follicular dermal sheath cells are from the dermal sheath in the lower part of the hair follicle.

3. The culture method according to claim 1, wherein the animal cell culture medium is Dulbecco's modified Eagle medium supplemented with 1% to 30% serum (DMEM10).

4. The culture method according to claim 1, wherein the hair follicular dermal sheath cells are cultured with other cells capable of forming the hair follicle.

5. A culture method for differentiating hair follicular dermal sheath precursor cells into dermal sheath cells and proliferating the cells, which comprises culturing the hair follicular dermal sheath precursor cells in an animal cell culture medium supplemented with platelet-derived growth factor AA (PDGF-AA) and fibroblast growth factor 2 (FGF2).

6. The culture method according to claim 5, wherein the hair follicular dermal sheath precursor cells are from the dermal sheath in the upper part of the hair follicle.

7. The culture method according to claim 5, wherein the animal cell culture medium is Dulbecco's modified Eagle medium supplemented with 1% to 30% serum (DMEM10).

* * * * *